(12) United States Patent
Wijetillake et al.

(10) Patent No.: US 11,724,107 B2
(45) Date of Patent: Aug. 15, 2023

(54) COCHLEAR IMPLANT SYSTEM WITH IMPROVED ELECTRODE SELECTION SCHEME

(71) Applicant: Oticon Medical A/S, Smørum (DK)

(72) Inventors: Aswin Adris Wijetillake, Smørum (DK); Simon Krogholt Christiansen, Smørum (DK); Pierre Stahl, Vallauris (FR); Dan Gnansia, Vallauris (FR); Manuel Segovia Martinez, Vallauris (FR)

(73) Assignee: Oticon Medical A/S, Smørum (DK)

( * ) Notice: Subject to any disclaimer, the term of this patent is extended or adjusted under 35 U.S.C. 154(b) by 98 days.

(21) Appl. No.: 16/919,551

(22) Filed: Jul. 2, 2020

(65) Prior Publication Data
US 2021/0001123 A1 Jan. 7, 2021

(30) Foreign Application Priority Data
Jul. 5, 2019 (EP) ..................................... 19184585

(51) Int. Cl.
*A61N 1/05* (2006.01)
*A61N 1/36* (2006.01)
*H04R 25/00* (2006.01)

(52) U.S. Cl.
CPC ....... *A61N 1/36038* (2017.08); *A61N 1/0541* (2013.01); *H04R 25/75* (2013.01); *H04R 2225/49* (2013.01)

(58) Field of Classification Search
CPC .............. A61N 1/36038; A61N 1/0541; A61N 1/36036
See application file for complete search history.

(56) References Cited

U.S. PATENT DOCUMENTS

| 2009/0177247 A1* | 7/2009 | Neal ................... A61N 1/36038 607/57 |
| 2011/0004274 A1* | 1/2011 | Schleich ............ A61N 1/36038 607/57 |

FOREIGN PATENT DOCUMENTS

| EP | 2 964 319 A1 | 1/2016 |
| WO | WO 2014/135203 A1 | 9/2014 |
| WO | WO 2018/106567 A | 6/2018 |

* cited by examiner

*Primary Examiner* — Michael J D'Abreu
(74) *Attorney, Agent, or Firm* — Birch, Stewart, Kolasch & Birch, LLP

(57) ABSTRACT

The invention relates to a cochlear implant system comprising a microphone unit configured to receive an acoustical signal and transmit an audio signal based on the acoustical signal, a processor unit configured to receive the audio signal and process the audio signal into a plurality of electrode pulses, an electrode array including a plurality of electrodes configured to stimulate auditory nerves of a user of the cochlear implant system based on the plurality of electrode pulses, and wherein the processor unit is configured to assign an importance value to one or more electrodes of the plurality of electrodes, wherein each of the importance values is determined based on a status of an electrode pulse assigned to the respective electrode, select a main set of electrodes of the plurality of electrodes during a time window, where the importance value of each of the selected electrodes of the main set of electrodes is larger or equal to an importance threshold value, activate the electrodes of the main set of electrodes to stimulate auditory nerves based on the electrode pulses of the plurality of electrode pulses, and reserve the electrodes of the main set of electrodes into a reserved mode during a reservation period.

20 Claims, 9 Drawing Sheets

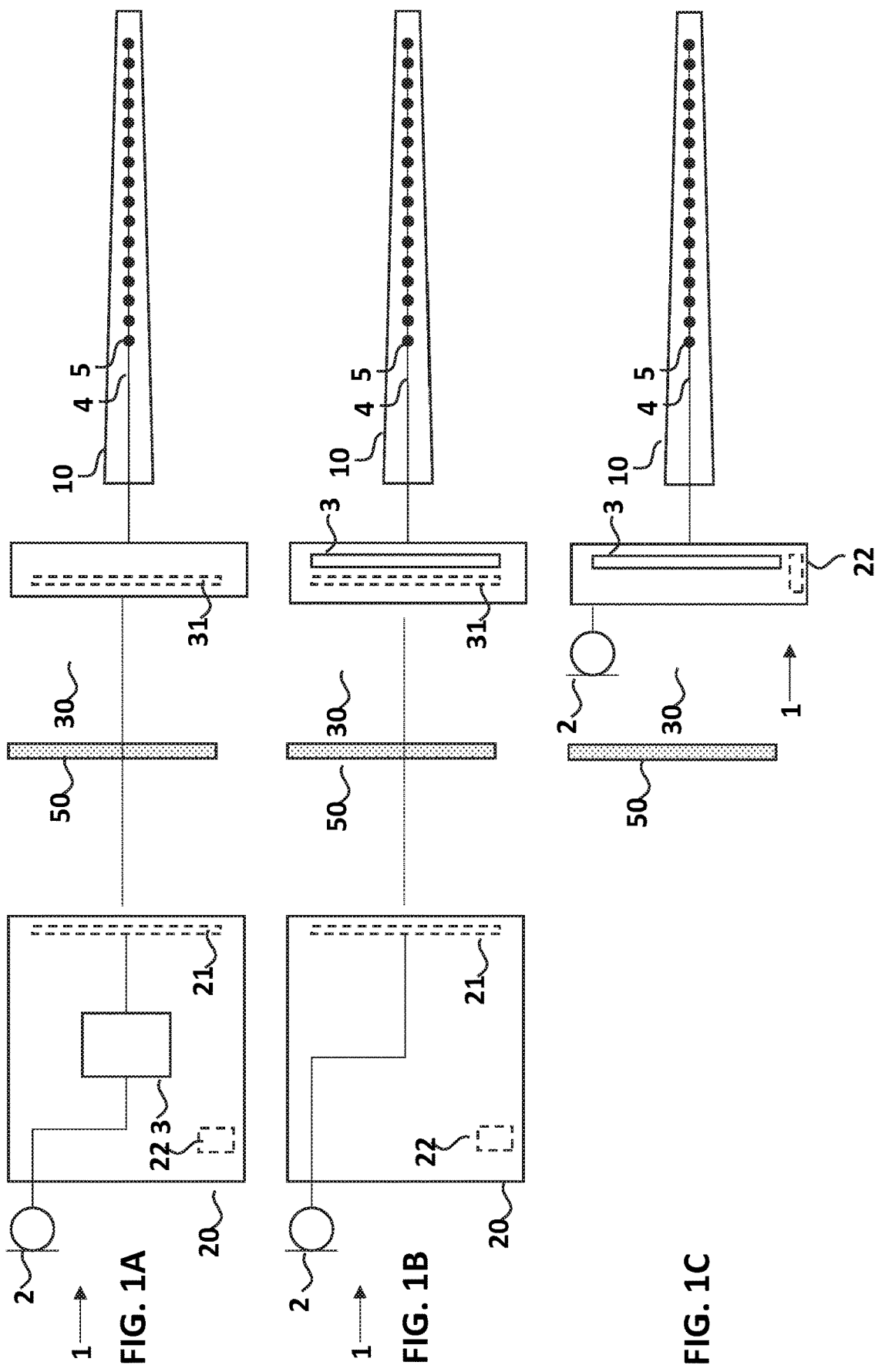

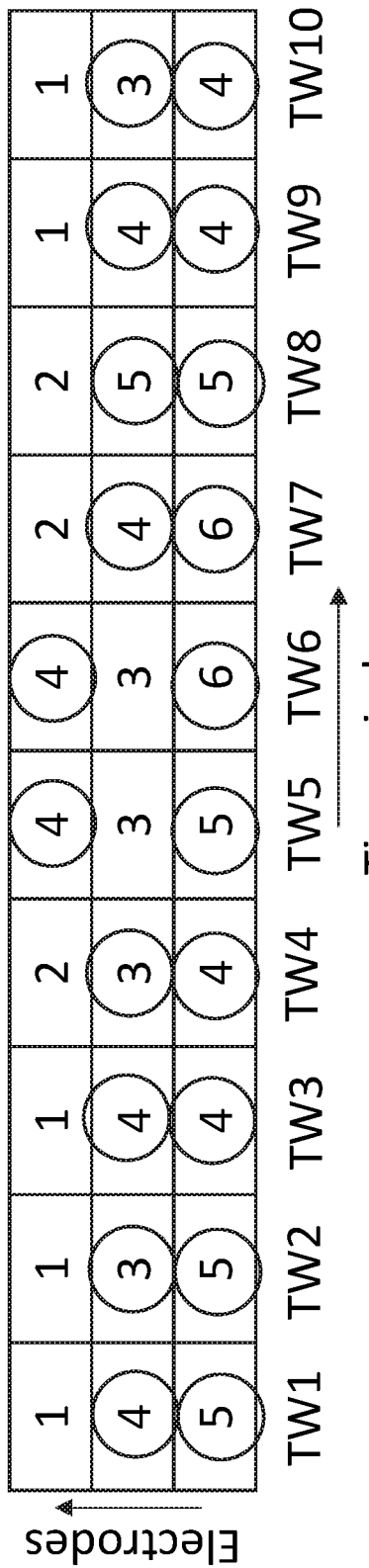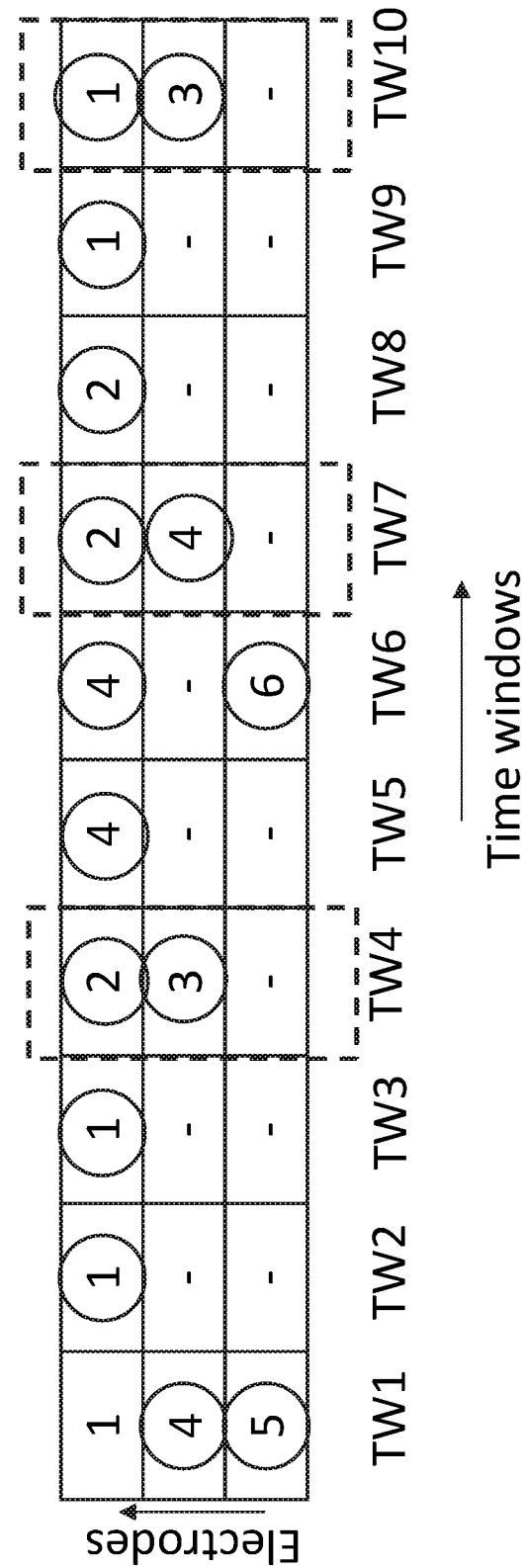

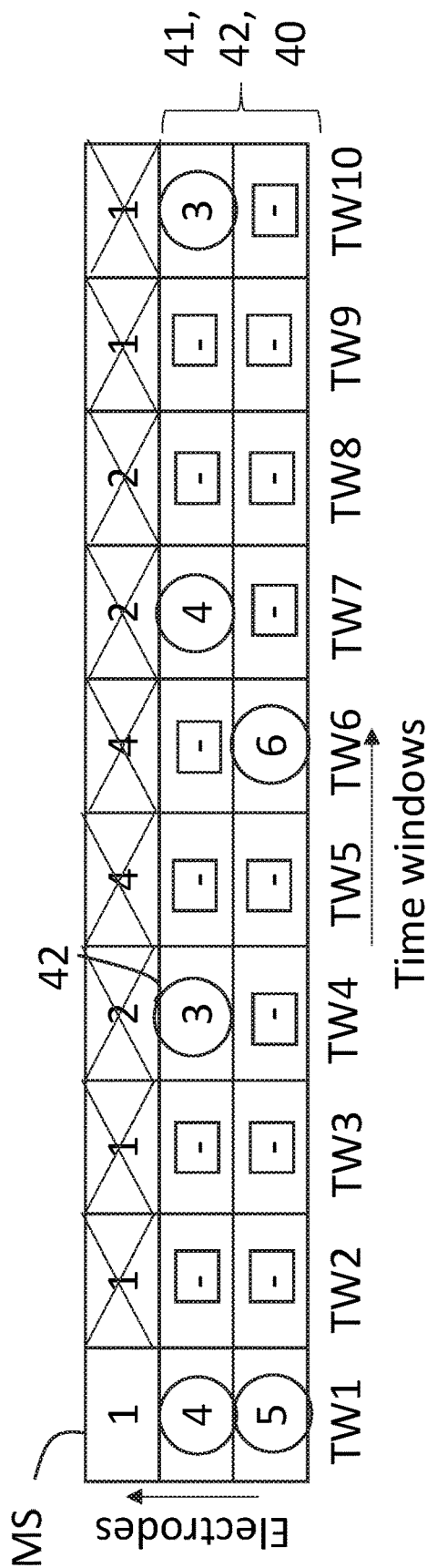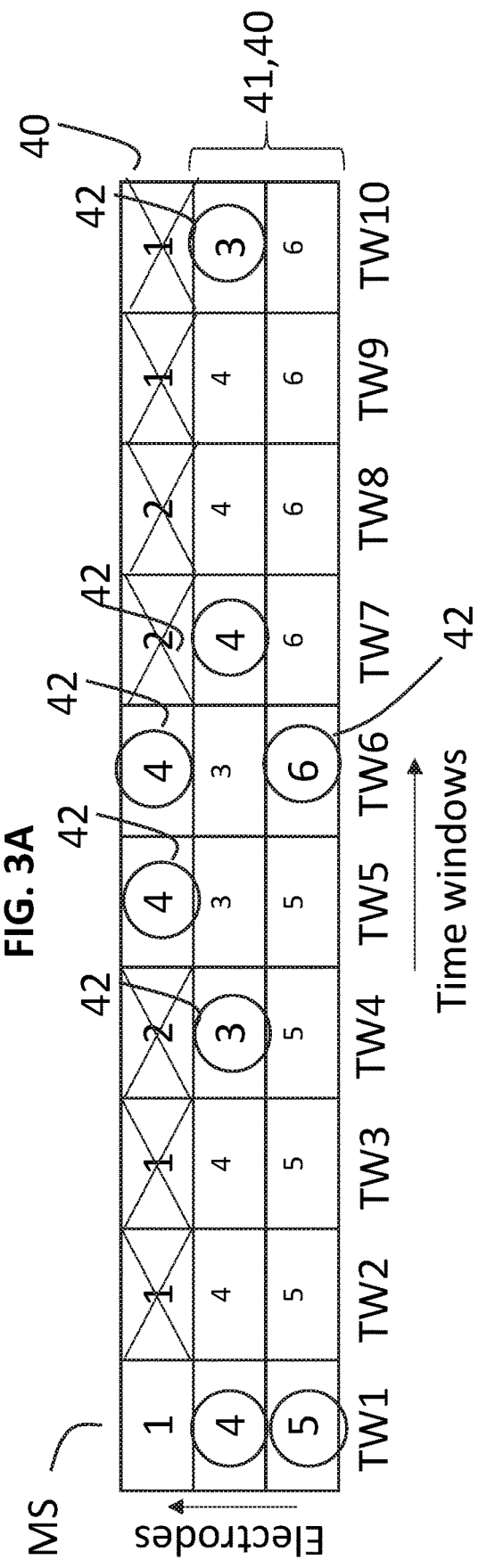
FIG. 3A
FIG. 3B

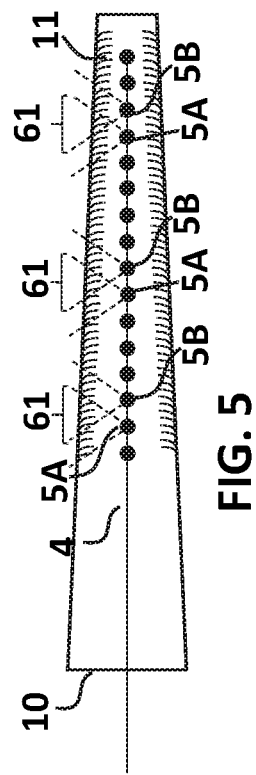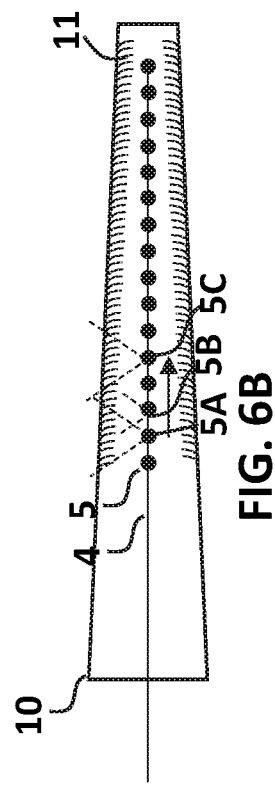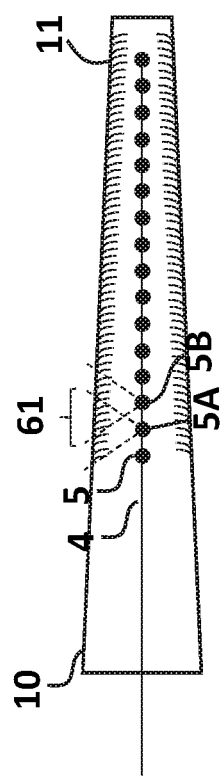

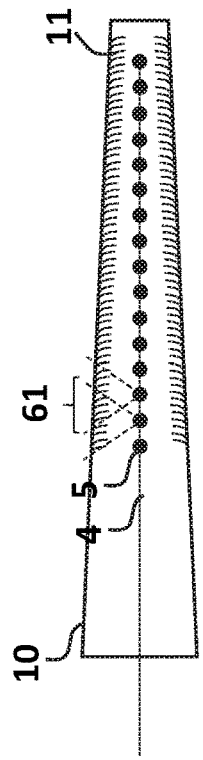
FIG. 7A
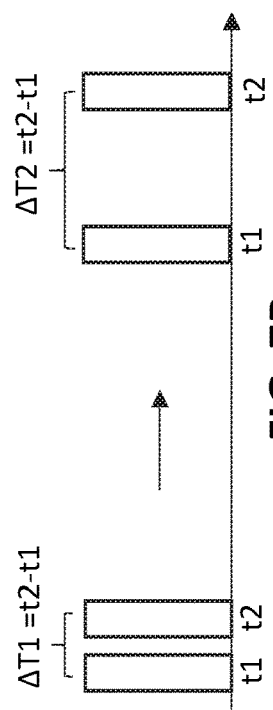
FIG. 7B
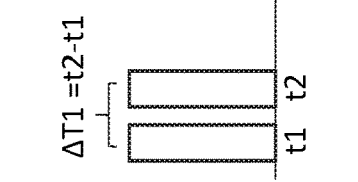
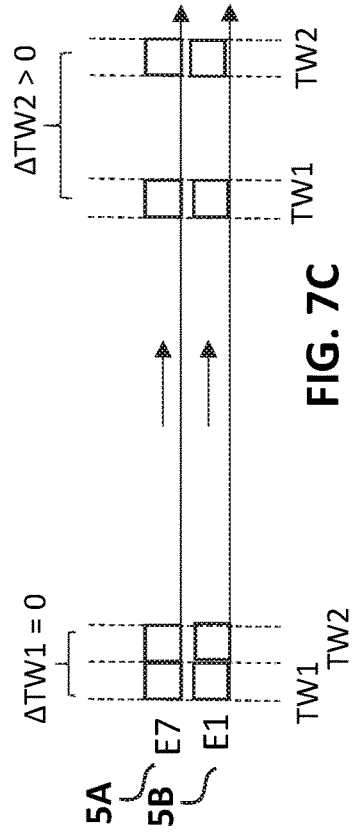
FIG. 7C

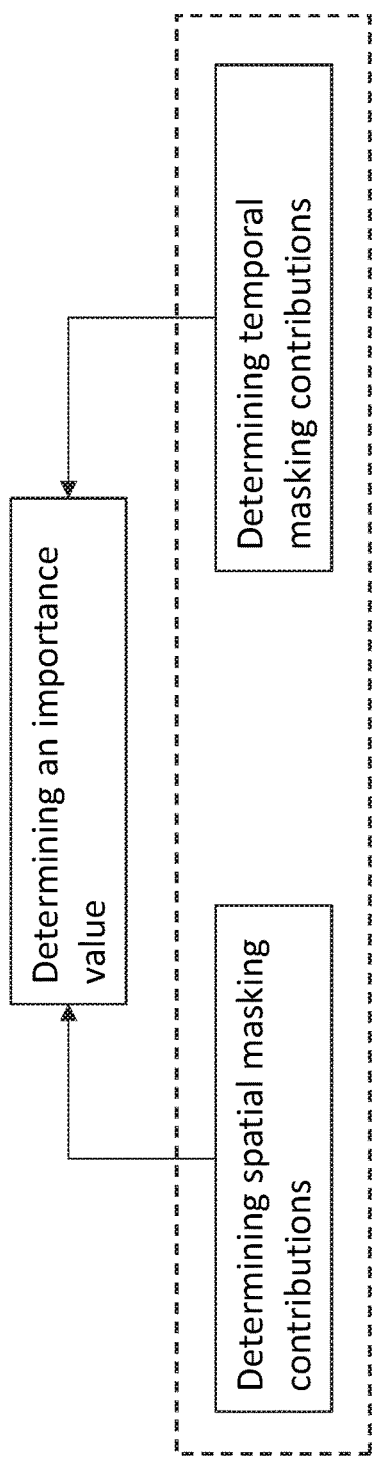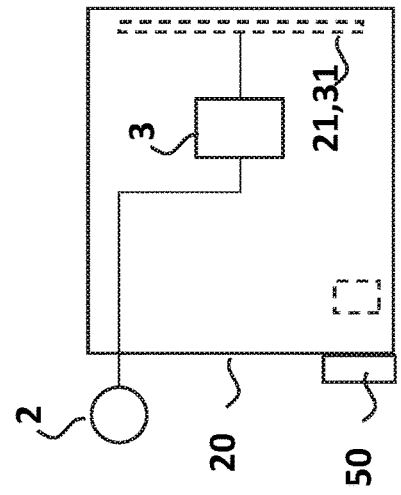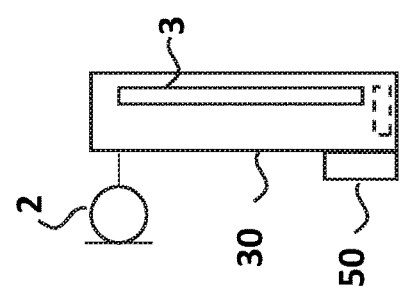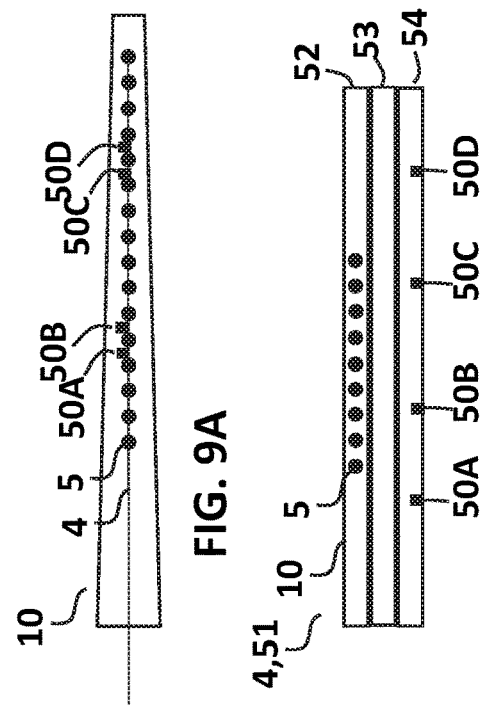

COCHLEAR IMPLANT SYSTEM WITH IMPROVED ELECTRODE SELECTION SCHEME

TECHNICAL FIELD

The disclosure relates to a cochlear implant system with an improved electrode selection scheme.

BACKGROUND

One major function of the cochlea in a normal (acoustic) hearing system is to spectrally decompose incoming acoustic signals and encode the resulting spectral components as neural excitation of the auditory nerve. The spectral decomposition and neural encoding are performed tonotopically along the length of the cochlea, and the spectral resolution can be modelled by a filter-bank. Multi-channel/electrode cochlear implant (CI) systems also perform a spectral decomposition and convert the resulting spectral components to electric current pulses, i.e. electrode pulses, that are delivered directly to the auditory nerve from tonotopically-mapped electrodes inserted within the cochlea. Ideally, the current electrode pulses delivered by a given electrode should selectively stimulate the same population of nerve fibres as would be recruited in a normal acoustic hearing system, for the same acoustic input signal. In practice, however, there relatively small number of electrodes available on current implants (between 12 to 22) and those electrodes typical produce broad current fields that elicit neural responses in substantially broader clusters of nerve fibres. This results in both poorer spectral resolution and substantial overlap in excitation elicited by different electrodes. Such excitation overlap produces significant across-electrode interferences whereby stimulation on one electrode disrupts the neural excitation elicited by another.

To mitigate the effect of across-electrode interferences, a number of CI coding strategies employ 'N-of-M' type channel selection methods to limit the number of stimulating electrodes in a given time window (i.e. an epoch of time), to a subset (N) of the total number of available electrodes ($N_{avail}$). In such schemes, the N electrodes containing 'events' (i.e. pulses or any spectro-temporal signal feature from which electrode pulses are ultimately derived) that convey the most 'important' information from the underlying acoustic input signal in a given time window are selected, and the remaining electrodes are deactivated so as to ensure that when output by the implant, the most important pulses are presented with minimal interference from stimulation on electrodes that do not encode important information. most important events are encoded with minimal interference from stimulation on electrodes that do not encode important events. Such methods may also employ an importance threshold to discard events that do not meet a baseline importance criterion, before applying the N-of-M selection. Criteria for assessing electrode event importance may be based on (but not limited to) energy, psychophysical masking, the periodicity in the underlying acoustic signal, signal coherence across channels and ears, etc.

The 'N-of-M' type electrode or channel selection is often employed in sound coding strategies that generate electrode pulses or events at a rate that is constant over-time and across electrodes. In such systems, the time windows within which N-of-M selection is performed are set to allow an equal number of events (i.e. electrode pulses) to be present on each electrode or channel. In such a case, no electrode or channel enjoys a selection advantage at any given time due to the rate at which events occur. However, when sound coding strategies are instead based on events that occur at rates that vary over-time and across channels, channels with higher event rates may receive a selection advantage over low-rate channels by virtue of containing more events in the time windows within which N-of-M selection is executed. The present described issue is illustrated in FIG. 2A and FIG. 2B for a fixed and variable-rate strategy, respectively; although modern CI systems typically employ N values between 8 to 12 for M values of 16 to 22, FIGS. 2A and 2B described a simplified scenario where N=2 and M=3. Both stimulation strategies are applied to the same hypothetical acoustic signal; the importance of channel during each time window of the underlying acoustic input signal is identical between coding strategies but the generation of events in response to that input signal differs. The abscissa on these panels denotes the time window index, i.e. the time window where one or more channels are being evaluated and selected, the ordinate denotes the channel index, and the values in each cell denotes an importance value of a hypothetical event. For the fixed-rate strategy, i.e. FIG. 2A, an event is present on each channel in each time window, and the selection method is able to test the importance of each channel or electrode against the others within any given time window. The channel or electrode with the most important event is therefore selected within all epochs.

Critically, since the selection scheme is impacted only by the importance value of an electrode or a channel, channels comprising unimportant/noisy information are NOT selected in any given time window. In contrast, in FIG. 2B, events are present in fewer time windows on the lower-rate channels than on the higher-rate channels for the variable-rate strategy. This leaves the high-rate channels essentially unchallenged during the selection procedure in some time windows. As such, a standard 'N-of-M' type will select the high-rate channels by default whenever an event is not present on the lower-rate channels. The overall coding strategy will thus code events on high-rate electrodes more frequently even if those events reflect unimportant/noisy information that may be perceived by the listener, and that may interfere with information on more important electrodes. This issue could be particularly detrimental for more practically relevant values of N and M than those in the present example (e.g. N=8, M=20), and is applicable for sound coding strategies that derive pulses from acoustic features that are unrelated to the underlying acoustic content importance.

SUMMARY

Throughout the description 'channel' and 'electrode' are used interchangeably, and 'event' and 'pulse' are used interchangeably.

An aspect of the present disclosure is to provide a cochlear implant system aiming for overcoming the mentioned disadvantages with the above described known solution.

An aspect of the present disclosure is to provide a cochlear implant system including an electrode selection scheme which prevents potentially unimportant/noisy information being unduly advantaged by higher event rates.

An aspect of the present disclosure is to provide a cochlear implant system including an electrode selection scheme that minimizes the amount of cross-electrode interference, the resolution of spectral components from the audio signal that are encoded by pulses delivered by electrodes on the implant.

The aspect of the present disclosure is achieved by a cochlear implant system comprising a microphone unit configured to receive an acoustical signal and transmit an audio signal based on the acoustical signal, a processor unit configured to receive the audio signal and process the audio signal into a plurality of electrode pulses, an electrode array including a plurality of electrodes configured to stimulate auditory nerves of a user of the cochlear implant system based on the plurality of electrode pulses.

The aspect of the present disclosure is achieved by a cochlear implant system comprising a microphone unit configured to receive an acoustical signal and transmit an audio signal based on the acoustical signal, a processor unit configured to receive the audio signal and process the audio signal into a plurality channels that are then used to generate a plurality of electrode pulses, an electrode array including a plurality of electrodes configured to stimulate auditory nerves of a user of the cochlear implant system based on the plurality of electrode pulses.

The processor unit may be configured to assign an importance value to one or more channels of the plurality of channels, or one or more electrodes of the plurality of electrodes, wherein each of the importance values may be determined based on a status of an electrode pulse assigned to the respective channel/electrode.

The status of the electrode pulse may be a measure of a parameter/feature of the electrode pulse which could include an estimated pulse energy level within a subset of frequencies of the frequency range of the electrode pulse.

The parameter/feature of the electrode pulse may include an estimated signal-to-noise ratio of the sampled audio signal within a subset of frequencies of the frequency range of the electrode pulse.

The parameter/feature of the electrode pulse may include a periodicity in the audio signal within a subset of frequencies of the frequency range of the electrode pulse, an audio coherence across the electrodes of the plurality of the electrodes and/or audio coherence across a second electrode array of another cochlear implant system.

The processor unit may further be configured to select a main set of electrodes of the plurality of electrodes during a time window, i.e. an epoch analysis frame, where the importance value of each of the selected electrodes of the main set of electrodes is larger or equal to an importance threshold value. The importance threshold value may for example be the maximum of the Nth highest electrode importance value or an absolute minimum importance value. The importance threshold value may for example be:
- a minimum allowable masking-weighted energy/charge/level value (resulting in fewer electrodes being activated to stimulate the auditory nerve),
- a minimum signal-to-noise ratio in the acoustic signal from which an electrode pulse is derived,
- a minimum estimated pulse energy level of an electrode pulse,
- a minimum value of an auto-correlation amplitude of the underlying acoustic signal, or
- a minimum interaural coherence value of the underlying acoustic signals received at the two ears.

The main set of electrodes are selected in a first time window of a plurality of time windows, where a subset of main electrodes or the plurality of electrodes may be selected during one or more other time windows of the plurality of time windows. The first time window is predecessor to the other time windows of the plurality of time windows.

The processor unit may further be configured to activate the electrodes of the main set of electrodes to stimulate auditory nerve based on the electrode pulses of the plurality of electrode pulses, and reserve the electrodes of the main set of electrodes into a 'reserved' mode during a 'reservation' period.

The processor unit is configured to activate the electrodes by transmitting an electrode pulse of the plurality electrode pulses to the respective electrodes.

The processor unit may include an electrode selection scheme which includes the steps of assigning the importance value to one or more electrodes, selecting one or more electrodes to the main set of electrodes, and reserving those electrodes of the main set of electrodes into a reserved mode during a reservation period.

In the proposed electrode selection scheme each electrode may enter a reserved mode for a duration, i.e. a reservation period, after an electrode pulse on that electrode has been selected. While in a reserved mode, that electrode will influence electrode selection during subsequent (future) epochs, i.e. time windows, regardless of whether an electrode pulse is present on that electrode in those time windows.

The duration of the reserved mode can be constant or vary across time and electrodes, and can be assigned either statically or adaptively. For example, the reservation period on a given electrode could be statically assigned to the inverse of the channel centre-frequency of an electrode or adaptively assigned to the inverse of a short-term estimate of frequency of a key spectral feature in the acoustic signal. During instances when a new electrode pulse arrives on an electrode that is already in a reserved mode, the reservation mode of that electrode could be deactivated, and the electrode would compete to be selected again by the N-of-M scheme. Alternatively, if an electrode pulse, i.e. an event, arrives on an electrode that is already in reserved mode, a check could be made to see if that electrode would be selected if it had to compete for selection by the N-of-M scheme. If it would be selected, that electrode pulse would then be selected, and the electrode would enter its reserved mode again. If not, the electrode pulse could be ignored, and the electrode could remain in its current reserved mode until that mode expires, i.e. expiration of the reservation period. Alternatively, an electrode could maintain a reserved mode until the next occurrence of an electrode pulse on that electrode. In each time window, the $N_k$ electrodes with the highest importance values and electrode pulses are selected, where the number $N_k$ of selected electrodes can vary across the time windows depending on the number of non-stimulating electrodes in reserved mode and $N_k \leq N$, where N is a subset of electrodes of the total number of available electrodes.

The reservation period may be different or the same for each of the electrodes of the main set of electrodes during the time window and/or during the coming time windows.

The reservation period may be equal or longer than the time window.

The determined reservation period for each of the electrodes may be based on the frequency content of each of the electrodes or the electrode pulses. For example, electrodes with higher frequency content will generate pulses more often than low frequency electrodes. This would give the electrodes with higher frequency content an undue advantage over the electrodes with lower frequency content. This is avoided by determining the reservation period for each of the electrodes based on the frequency content.

If the electrode being selected is reserved and has an assigned electrode pulse, the reservation period of that electrode is renewed.

In the case where two or more active electrodes pulses have the same importance metric value, but only a subset of those electrodes can be selected, a 'tie-breaker' importance value could be used to select that subset. The tie-breaker importance value must be different from the importance value, previously defined, and could include: channel center frequency, pulse energy, Signal-to-noise-ratio, interaural coherence, periodicity, etc.

Within a time window an electrode could be assigned with both an importance value and a tie-breaker importance value.

Within a time window the electrode could be assigned with a tie-breaker importance value, wherein the tie-breaker importance value must be different from the importance value assigned to the electrode in a previous time window.

The processor unit may be configured to assign a tie-breaker importance value to the electrodes of the plurality of electrodes, where the tie-breaker importance value is different from the assigned importance value. The processor unit may be configured to select one or more electrodes being part of the tie-breaker, where the tie-breaker importance value of each of the selected electrodes is larger than or equal to the importance threshold value of the respective electrodes. The tie-breaker importance value could include: channel center frequency, pulse energy, Signal-to-noise-ratio, interaural coherence, periodicity, and/or cross-electrode interference.

The proposed selection scheme of electrode could be applied to either unilateral or bilateral sound coding strategies, where electrodes in the latter can be assessed and selected by comparing stimulation signals provided at two ears of the user.

The cochlear implant system may comprise a memory unit which is configured to store the importance values of the one or more electrodes, for the current time window and possibly for one or more (or no) previous time windows. The processor unit is configured to update the importance value continuously based on changes to the status of an electrode pulse assigned to the respective electrode.

The memory unit is connected to the processor unit and configured to receive and transmit the importance value of the one or more electrodes.

The processor unit may be configured to select a subset of electrodes of the main set of electrodes during the reservation period and no other electrodes of the plurality of electrodes are allowed to be selected, and wherein each of the electrodes of the subset of electrodes has an importance value that is larger or equal to the importance threshold value, and wherein the processor unit is configured to activate the electrodes of the subset of electrodes to stimulate auditory nerves based on the electrode pulses of the plurality of electrode pulses.

The processor unit may be configured to select a subset of electrodes of the plurality of electrodes, where each selected electrode of the subset of electrodes is assigned with an electrode pulse and with an importance value being larger or equal to the importance threshold value, and where the subset of electrodes includes a maximum number of electrodes $N_k$ determined by N (the maximum allowable active electrodes within a time window, i.e. an epoch) minus the number of electrodes do not currently have an active pulse but are in the reserved mode. In other words, the electrode array or the plurality of electrodes includes in total M number of electrodes, and $N_k$ of M is allowed to be active during a time window k, where $N_k$ can differ across time windows. If a 'soft' reservated mode is employed, the electrodes in reserved modes will only block an electrode pulse-conveying electrode if the computed importance value of the event does not exceed an importance value assigned to the reserved electrode.

This may be preferable for preventing high importance events from being blocked by reserved electrodes that previously entered the reserved mode with a lower importance value. The importance value of an electrode in a reserved mode could be assigned and held constant at the instance the channel/electrode was reserved or could vary over-time (e.g. decay as time passes). Alternately, the importance value of a reserved electrode at any given time could be computed independently from the importance value computed at the time the electrode became reserved.

Rather than holding the importance value of an electrode constant when that electrode enters the 'soft' reserved state, the importance value of that electrode could continue to be updated in each time window while that electrode is reserved. The electrode would be selected to enter the reservation mode during a time window when both an electrode pulse was present on that electrode, and the electrode pulse had an importance value equal to or larger than the importance threshold value. By updating the importance value of the reserved electrode in subsequent time windows, the ability of that electrode to prevent the selection of other active electrode pulse carrying electrodes from being selected would be dependent on the importance value of the (acoustic) content of the channel for that electrode within that current time window rather than the importance value during the time window the electrode entered the reserved mode.

The processor unit may be configured to select a subset of electrodes of the plurality of electrodes (i.e. includes electrodes which are not part of the main set of electrodes) and/or of the main set of electrodes during the reservation period, wherein each the electrodes of the subset of electrodes has an importance value that is larger or equal to the importance threshold value, and wherein the processor unit is configured to activate the electrodes of the subset of electrodes to stimulate auditory nerves based on the electrode pulses of the plurality of electrode pulses.

The importance threshold value is determined as following determining a minimum importance threshold value, determining a minimum importance value of the subset and/or main set of electrodes, determining the importance threshold value as being equal to the minimum importance value, if the minimum importance value is larger or equal to the minimum importance threshold value, or determining the importance threshold value as being equal to the minimum importance threshold value, if the minimum importance value is smaller than the minimum importance threshold value.

For example, the importance value may be based on noise level, and the cochlear implant system may define an acceptable noise level of 40 dB SPL. Each electrode which has a noise level above this acceptable level, plus a noise error margin (+3 dB) is not selected. Likewise, a system may also have a noise floor of 20 dB SPL. Each electrode with signal levels below the noise floor will not be selected.

The processor unit may be configured to replace an electrode of the main set of electrodes with a new electrode where the importance value of the replaced electrode is less than the importance threshold value and where the importance value of the new electrode is equal or larger than the importance threshold value. Thereby, a more important electrode pulse may be selected over a less important electrode pulse which were in reserve mode. The cochlear implant system becomes more flexible to sudden changes in the audio signal, for example, in noisy situations, where sudden changes of the importance value of each electrodes may appear during the reservation period The processor unit may be configured to update the main set of electrodes by adding a new electrode of the plurality of electrodes to the main set of electrodes where the importance value of the new electrode is larger or equal to the first threshold importance value.

The number of electrodes of the main set or the subset of electrodes may not go beyond the total number of available electrodes ($N_{avail}$).

The processor unit may be configured to update the main set of electrodes by renewing the reservation period of an electrode of the main set of electrodes when a new pulse generating event occurs on that electrode with an importance value that is greater than or equal to the importance threshold value.

The processor unit may be configured to update the main set of electrodes by removing an electrode from the main set of electrodes when the reservation period of that electrode has expired, and before that reservation period could be renewed.

The processor unit may be configured to sample the audio signal within a frequency range, and wherein the status of the electrode pulse of the plurality of electrode pulses includes an estimated pulse energy level within a subset of frequencies of the frequency range, an estimated signal-to-noise ratio of the sampled audio signal within a subset of frequencies of the frequency range, a periodicity in the audio signal within a subset of frequencies of the frequency range, audio coherence across the electrodes of the plurality of the electrodes, and/or an audio coherence across a second electrode array of another cochlear implant system.

The status of the electrode pulse may be a measured parameter of the plurality of electrodes which may be performed during fitting and/or during operation of the cochlear implant system. The pulse energy level of each electrode is determined by the processor unit alone or based on measurements performed by a sensor or the electrode array. The measurement sensor is connected to the processor unit and configured to measure the stimulation provided by the electrodes. The measured stimulation may include the pulse energy level and/or a noise estimate. The measurement signal is transferred to the processor unit. The measurement signal includes for example the pulse energy level and/or the noise floor level. The processor unit may be configured to determine a signal-to-noise ratio of an electrode based on the measurement signal. The noise floor level of each electrodes is measured by the measurement sensor when no electrode pulses are applied to the respective electrodes. The periodicity in the audio signal and the audio coherence are determined by the processor unit.

The importance values of the electrodes of the subset of electrodes are larger than the importance values of the electrodes not being selected.

The importance threshold value may be determined such that the main set and/or the subset of electrodes includes a number of active electrodes of between 2 to 5 electrodes, 2 to 10 electrodes, 2 to 15 electrodes, 2 to 25 electrodes or above 25 electrodes.

The ideal maximum number of stimulating electrodes, N, within a given time frame can vary across patients and across stimuli.

For example, for patients with low amounts of across-electrode interference, i.e. spread-of-excitation and spatial masking, it may be possible to stimulate a greater number of electrodes without introducing significant electrode interactions in comparison to patients with high mounts of across-electrode interference. Conversely, patients who suffer high amounts of spread-of-excitation may be being stimulated on too many electrodes and thus experience significant electrode interactions; reducing the number of active electrodes could also reduce the power consumption of the cochlear implant system for those patients.

Furthermore, if there is significant variability in the across-electrode interference (within a patient), an optimal number of active electrodes may actually vary depending on the specific selection of electrodes. It is therefore beneficial to determine the optimal N electrodes by:

fitting and tailoring the number of active electrodes to an individual patient/user, and/or adapting the number of active electrodes on a short-term basis depending on the selected electrodes.

A spread-of-excitation could be estimated on each electrode for a given patient of the cochlear implant system. This could be achieved, for example, by using electrically evoked compound action potential (eCAP) measurements. Using standard eCAP measurement, techniques, a spread-of-excitation function can for example be estimated for a given electrode by stimulating on that electrode, i.e. stimulation electrode, and measuring the ECAP response on each electrode of the electrode, i.e probe measurement electrode. Thereby, a spread-of-excitation function may be determined including the measured ECAP response as a function of the electrode number for a given stimulation electrode. The measured ECAP response may be expressed as a normalized ECAP magnitude of the measured ECAP response which reflects the amount of spatial masking contribution each measurement electrode experience in response to stimulation provided by the stimulation electrode, i.e. higher ECAP magnitudes indicate higher amounts of spatial masking contribution. A metric describing the spread width of spatial masking contribution for the stimulation electrode could then be defined to include, for example, the 3 dB bandwidth of the function or a multiple of the function's standard deviation, etc. A spread-of-excitation function and spread-width metric could then be computed for each electrode, and an optimal number of active electrodes could then be computed based on the spread-of-excitation function and the spread-width metric for each electrode so as to produce an allowed amount of spatial masking contribution, i.e. electrode interference. One possible method to compute the number of active electrodes is given by:

$$N_{N\text{-}of\text{-}M} = \text{round}\left(\frac{N_{array}}{\frac{1}{N_{array}}\sum_{p=1}^{N_{array}} w(p)}\right),$$

where $N_{array}$ gives the number of electrodes on the electrode array, the expression in the denominator gives the average spread-width of all electrodes and round( ) describes the process of rounding the outcome of the equation to an integer value (up, down or closest).

The method for determining the optimal number of active electrodes could be performed automatically by an implant fitting software, whereby one or more eCAPs is measured for every combination of stimulation electrode and measurement electrode to produce the on the spread-of-excitation functions for each electrode.

The spread-of-excitation function and/or spread-width metric of each electrodes may be stored in the memory unit of the cochlear implant system.

The processor unit may be configured to compute an optimal number of active electrodes for a given audio signal based on the spread-of-excitation function and the spread-width metric for each electrode so as to produce an allowed amount of spatial masking contribution, i.e. electrode interference.

The optimal number of active electrodes may vary depending on the specific electrodes of the electrode array that are selected. Electrodes with broader spread-widths are selected in a given time window, i.e. an epoch, the optimal number of active electrodes could be lower than when electrodes with narrower spread-widths are chosen. Electrodes could be iteratively selected within a given time window until the summed spread-width of those selected electrodes exceeds a pre-defined maximum allowed summed spread-width. Other parameters, such as pulse energy of an electrode for example, could also be considered when computing the summed spread width, and by weighting the spread-width of each electrodes by those parameters. Furthermore, establishing predefined maximum summed spread-widths for specific group of adjacent electrodes of the electrode array (i.e. specific regions of the electrode array), and iteratively selecting electrodes of the group of adjacent electrodes until the allowed summed spread-width for that group is exceeded. In this case, the optimal value of active electrodes would vary both across the electrode array and locally in different groups of adjacent electrodes of the electrode array. This may have the benefit of further reducing the amount of electrode interaction that occurs between stimulating electrodes of the electrode array.

A fitting software could employ current spread models that predict the spread-of-excitation functions on each electrode, and that can be fitted to the patient of the cochlear implant system by collecting few eCAP measures of different stimulation electrodes of the electrode array. For example, if the spread-of-excitation on each electrode is assumed to be modelled by a specific function, e.g. a Gaussian function, the fitting software is configured to measure eCAPs on a subset of probe electrodes combinations, and then fit the assumed function using standard curve fitting methods. More complex models could also be employed. The use of such models may reduce the overall time needed to collect eCAP data, and thus the time required to determine the optimal amount of active electrodes during a clinical fitting session.

The spread-of-excitation function may include spatial masking contribution and/or temporal masking contribution.

The number of electrodes in the main set and/or the subset of electrodes may be determined by the method for determining the optimal number of active electrodes.

The fitting software may be part of a fitting system.

The importance value is determined based on the status of an electrode pulse assigned to a given electrode. The status of the electrode pulse of the plurality of electrode pulses may be determined by estimating a pulse energy level of the electrode pulse if the frequency of the electrode pulse is within a subset of frequencies of a frequency range. If the pulse energy level is increasing, then the importance value would also increase.

The status of the electrode pulse of the plurality of electrode pulses may be determined by estimating a pulse energy level of the electrode pulse and applying importance value which depends on the frequency range in the acoustic signal from which the electrode pulse was derived.

An electrode pulse with a high pulse energy level may indicate that the electrode pulse includes important information which may lead to enhanced perceptual ability of the user.

Thus, by selecting those electrodes which has an importance value larger than or equal to an importance threshold value, and where each importance value is determined based on the pulse energy level, then the user's perceptual ability is improved. The improved perceptual ability is provided by the cochlear implant system being able to select those electrode pulses that convey important information and neglect those electrode pulses which are assumed to include none relevant information, such as noise.

The status of the electrode pulse of the plurality of electrode pulses may be determined based on a signal-to-noise ratio of the sampled audio signal within a subset of frequencies of the frequency range, where if the signal-to-noise ratio of the sampled audio signal increases then the importance value also increases. The user's perceptual ability is further improved when selecting those electrode pulses which has the highest signal-to-noise ratio.

Thus, the user's perceptual ability will even more be improved by combining both pulse energy level and the signal-to-noise ratio in the determination of the importance value. By combining both the pulse energy level and the signal-to-noise ratio, the ability of the cochlear implant system to select those electrode pulses with important information has improved even more.

The status of the electrode pulse of the plurality of electrode pulses may be determined based on a periodicity in the audio signal within a subset of frequencies of the frequency range. The cochlear implant system is then configured to select those electrode pulses which includes audio information with a certain periodicity which will lead to an improved pitch perception of the user. The relation between pitch perception and periodicity is explained in *"Periodicity and pitch perception"*, Pierce, John R., Center for Computer Research in Music and Acoustics, Department of Music, Stanford University, Stanford, Calif. 94505, PACS number 43.66.MK, 43.66.Hg [WAY], and which is hereby incorporated by reference. The status of a pulse on an electrode may be determined by the coherence (max amplitude of the cross-correlation) between the audio signals received by two or more microphones, within the frequency range associated with the electrode. The microphones could be located on the same sound processor at the same ear or distributed over the sound processors at the two ears for a bilateral user (i.e. 'interaural coherence'). Higher coherence values suggest that the information conveyed by a pulse is more likely to be derived from sound coming from a single source direction (i.e. a single source) in space rather than multiple sources direction. Higher interaural coherence values further suggest that the binaural cues conveyed by a pulse are more to reflect one source direction rather than multiple directions. Therefore assigning importance based on coherence enhance the users ability to focus on a single sound in complex environment and, in the case of binaural coherence, enhance their ability to localize sounds in space.

The status of the electrode pulse of the plurality of electrode pulses may be determined based on across-electrode interferences, i.e. masking, imposed on an electrode pulse by other electrode pulses of the plurality of electrode pulses. For example, if an electrode pulse receives a large amount of masking from other electrode pulses, then the importance value of that electrode which includes the electrode pulse would be low, or, if an electrode pulse receives a small amount of masking from other electrode pulses, then the importance value of the electrode which includes the electrode pulse would be high. The status of the electrode pulse of the plurality of electrode pulses may then be determined based on the amount of masking received by the electrode pulse.

The status of the electrode pulse of the plurality of electrode pulses may be determined based on across-electrode interferences, i.e. masking, imposed on an electrode pulse by other electrode pulses of the plurality of electrode pulses. For example, if an electrode pulse imposes a large amount of masking to other electrode pulses, then the importance value of the electrode which includes the electrode pulse would be low, or, if an electrode pulse imposes a small amount of masking to other electrode pulses, then the importance value of the electrode which includes the electrode pulse would be high. The status of the electrode pulse of the plurality of electrode pulses may then be determined based on the amount of masking imposed by the electrode pulse.

The status of the electrode pulse of the plurality of electrode pulses may be determined based on a masking model of across-electrode interferences imposed on an electrode pulse by other electrode pulses of the plurality of electrode pulses.

Ideally, the electrode pulses delivered by a given electrode should selectively stimulate the same population of nerve fibres as would be the case in a normal acoustic hearing system, for the same acoustic input signal. In practice, however, the broad current fields generated with cochlear implant stimulation elicit neural responses in substantially broader clusters of nerve fibres, resulting in both poorer spectral resolution and substantial overlap in excitation elicited by different electrodes. This excitation overlap produces significant across-electrode interferences, i.e. masking, whereby stimulation on one electrode consumes some of the neural resources at the site of neighbouring electrodes, thus disrupting the neural excitation elicited by stimulation. Thus, by applying the masking model scheme to the determination of the importance value would result in that the cochlear implant system is configured to select those electrode pulses which results in a reduced cross-electrode interference. The advantage of doing this is an improved spectral resolution of the electrode pulses converted from the audio signal.

The status of the electrode pulse of an electrode of the plurality of electrodes can include a determined amount of across-electrode interference induced on the electrode pulse of the electrode by one or more electrode pulses of other electrodes of the plurality of electrodes based on the masking model scheme, wherein the masking model scheme comprising determining spatial masking contributions of each of the one or more electrode pulses of the other electrodes induced on the electrode pulse of the electrode based on a spatial separation between the electrode and each of the other electrodes. The effect of spatial separation on masking is affected by the stimulation level, e.g. higher stimulation levels cause more spread than low stimulation levels, and can vary between patients and between specific electrodes within a patient. The plurality of electrodes may be arranged in an order starting from electrode 1 to electrode N, and where a distance between the electrodes is determined based on the respective stimulation levels of the electrodes. For example, an electrode pulse with high stimulation level in comparison to low stimulation level will have a shorter distance to a neighbouring electrode.

The status of the electrode pulse of an electrode of the plurality of electrodes includes a determined amount of across-electrode interference induced on the electrode pulse of the electrode by one or more electrode pulses of other electrodes of the plurality of electrodes based on the masking model scheme, wherein the masking model scheme comprises determining temporal masking contributions of each of the one or more electrode pulses of the other electrodes induced to on the electrode pulse of the electrode based on a pulse time difference between a first time of the electrode pulse of the electrode and a second time of each of the one or more electrode pulses of the other electrodes, wherein the second time is preceding the first time. The first time and the second time are defined to be within the time window, or the first time could be defined within a first time window and the second time could be defined within the first time window or previous time windows. The amount of masking decays as the pulse time difference increases.

The masking model scheme may include both the determination of spatial masking contributions and the determination of temporal masking contributions. The advantage of applying the masking model scheme to the determination of the importance value is that the information transferred up the auditory nerve is maximized by only including the electrode pulses which impose less cross-electrode interference and which will contribute to the most perceptual effects and reducing power consumption.

The advantage of applying both the spatial masking contributions and the temporal masking contributions. Having spatial on its own will not take into account the order in which pulses arrive, and will not take into account the time difference between them. Having temporal effects on their own will take the pulse order and timings into account, but not the differences in electrode positions. Having both in the masking model scheme will therefore enable proper prediction of which pulses will be masked.

It is important to include temporal effects for CI users because pulses occur at discrete times. Pulses that arrive earlier will mask those that arrive later, but not the other way around.

The determined spatial masking contribution from each of the electrode pulses on the other electrodes may be multiplied by a temporal masking decay function that includes the pulse time difference between the pulse of the electrode and each of the pulses on the other electrode. For example, the electrode pulse may have a first time and a first other electrode pulse may have a second time, and the pulse time difference may be between the first time and the second time, and a second other electrode pulse may have a second time, and where the pulse time difference may be between the first time and the second time of the first other electrode pulse and/or between the first time and the second time of the second other electrode pulse. The temporal masking function may be fixed across all electrodes, may be vary across electrodes, or vary across pairs of electrodes.

The pulse time difference could be changed by adjusting the first time of the electrode pulse and/or the second time of the other electrode pulses. The adjustment of the first time and/or the second time may be based on the determined cross-electrode interference imposed on the electrode pulse and/or based on the determined cross-electrode interference induced by the other electrode pulses.

The pulse time difference could be changed by adjusting the timing between the first time window and the second time window or by changing the time length of the first time window and/or the second time window.

The changing of the pulse time difference may be done by the processor unit.

Adjusting the timing of the electrode pulses provides a way of reducing cross-electrode interference without the need of changing the spatial separation between the electrode pulses which may lead to acoustical artifacts. Thereby, the user will experience an enhanced perception in view of the application where only the spatial separation is changed for the purpose of reducing the cross-electrode interference.

The temporal masking decay function may include a time constant which may be either fixed or vary across the electrodes of the plurality of electrodes which would yield electrode specific decay functions. The decay functions could be determined through psychophysical and/or objective neurophysiological measures, such as Electrically Evoked Compound Action Potential (ECAP). The amount of masking imposed on a given electrode pulse could be computed using all preceding pulses that fall within the same time window, i.e. an analysis epoch, or could additionally consider pulses from previous time windows. The latter could be useful if the previous time windows are sufficiently shorter than the timescales over which masking decay occur. In that case, masking from previous pulses within the previous time windows could be included if the temporal masking factor has not yet decayed below a certain decay threshold, or the amount of masking (i.e. spatial masking multiplied by temporal decay factor) still exceeds a masking threshold. The advantage of including the temporal masking factor into the determination of cross-electrode interference is that The spatial masking contribution may be determined based on spatial masking functions for a given patient which could be derived directly by obtaining objective measurements (such as eCAP) or behavioural psychophysical measures. When using both methods, the procedure could be sped-up by using models of spatial masking that would fit the patient by collecting a smaller number objective or behavioural measurements. Using eCAP, the masking imposed on an electrode $e_{masked}$ by stimulation on an electrode $e_{masker}$, i.e. one electrode from the other electrodes, can be determined by stimulating on $e_{masker}$ and measuring the eCAP response using electrode $e_{masked}$. By iteratively varying the electrode $e_{masked}$, while keeping the stimulating electrode fixed on $e_{masked}$, the spatial masking function $MS(e_{masked}, e_{masker})$ caused by stimulation on $e_{masker}$ cancan then be derived. This be repeated for a multiple of stimulating electrodes to derive the masking functions associated with stimulation on each electrode. Alternatively, $MS(e_{masked}, e_{masker})$ may be determined, when using the 'masker-probe' eCAP method, by presenting the probe stimulus to $e_{masked}$ and the masking stimulus to $e_{masker}$ and by recording the eCAP response on $e_{masked}$ or on an adjacent electrodes. By repeating this process for different combinations of 'probe' and 'masker' electrodes, a full set of spatial masking functions can be determined. A multitude of behavioural psychophysical tests could be used to also determine spatial functions. An example of such a test could include stimulating on the electrode $e_{masker}$ at a fixed level and determining (using standard psychophysical methods), by stimulating on the electrode $e_{masked}$ with different levels, the minimum level required to detect the stimulus on $e_{masked}$ in the presence of the stimulation on $e_{masker}$. Once again, by iteratively varying the electrode of $e_{masked}$, while keeping $e_{masker}$ fixed, the spatial masking functions associated with stimulation on $e_{masker}$ can be derived.

The temporal masking contributions of each of the one or more other electrodes may be expressed by a temporal masking function. The temporal masking function can also be derived directly by obtaining objective or behavioural measures for a range of time differences between leading and lagging pulses. This process may be speed-up by fitting a model of temporal masking decay function using fewer numbers of measurements. The decay of masking with increasing pulse time difference can be determined with eCAP by varying the difference between the offset time of the stimulating electrode pulse and the time the eCAP response is measured. It can also be measured, when using the 'probe-masker' method, by measuring eCAPs with different intervals between masker and probe. Likewise, behavioural temporal masking tests could be run where a detection threshold level of a lagging pulse is measured, for a given leading pulse level, for different time differences. In both cases, the effect of both time and the spatial separation between the electrodes of the leading and lagging pulses can also be measured. For eCAP, the electrode and time at which the measurements are made could be varied. Likewise for the behavioural test, both the electrode and the timing of the lagging pulse could be varied.

The processing unit may be configured to control the cross-electrode interference in between the electrode pulses of the plurality of electrodes by changing the first time of the electrode pulse of the electrode and/or the preceding time of each of the one or more electrode pulses of the other electrodes. For example, if cross-electrode interferences is assumed to imposed a greater cognitive load on users, the cochlear implant system may include a sensor configured to measure cognitive load of the user, and thereby, based on the measurement signal including the measured cognitive load the processing unit is configured to control the cross-electrode interference. The sensor may be part of the electrode array, the implant part or an external part connected to the cochlear implant system. The sensor may include one or more electrode pads made of IrO2.

The processing unit may be configured to control the cross-electrode interference between the electrode pulses of the plurality of electrodes by applying a time delay between a first time window and a second time window, wherein in both of the time windows the processor unit is configured to select a subset of electrodes of the plurality of electrodes and/or to select electrodes of the main set of electrode of the plurality of electrodes.

The first time, the preceding times, and the time delay may be determined continuously by the processor unit.

The first time, the preceding times, and the time delay may be determined continuously by the processor unit based on a masking measure provided by the electrodes of the plurality of electrodes during fitting of the cochlear implant system and/or during operation of the cochlear implant system.

The processing unit may be configured to control the cross-electrode interference based on a subjective measure, such as a questionnaire, being introduced to the user via a graphical user interface. The user may receive one or more questions relating to the users perceivability of the generated stimulation provided to his/hers auditory nerves. The graphical user interface includes an input interface for receiving the user's answers to the questions. The processing unit may receive a command signal which determines the controlling of the cross-electrode interference. The command signal may be determined, based on the questionnaire and the answers from the user, by an external server or a computer connected to the graphical user interface. The command signal may for example include the amount of changing of the pulse time difference and/or the changing of the time windows and/or the delay between the time windows, such as the first time window and the second time window. The graphical user interface may be part of a smartphone, a tablet, or any computational device. The input interface may be separated from the graphical user interface.

The processor unit may be configured to determine the status of an electrode pulse, by determining a masking adjusted energy/charge/level including an estimated pulse energy/charge/level of the electrode pulse minus the amount of across-electrode interference induced to the electrode pulse from the one or more electrode pulses of the other electrodes.

The processor unit may be configured to determine the status of an electrode pulse, by determining a masking-weighted energy/charge/level that comprises the estimated pulse energy/charge/level of that electrode pulse multiplied by an across-electrode interference scaling factor (i.e. between 0 and 1) that includes an effective energy/charge/level of the electrode pulse after considering the amount of across-electrode interference induced to the electrode pulse from the one or more electrode pulses of the other electrodes, whereby the effective energy/charge/level provides an estimate of the energy/charge/level that would yield the same amount of activity in the auditory nerve as the pulse of interest, if across-electrode interference was absent.

These masking adjusted energy/charge/level would essentially reflect the amount of information transfer that each electrode pulse would be able to transmit up the auditory nerve, thus the salience/strength of the perceptual effect it would elicit, given the level and relative timing the pulse on each electrode. Since the parameter/feature of interest is not directly related to masking-weighted energy/charge, channels/electrodes with high parameter/feature values may not necessary have their information reliably transferred up the auditory nerve due to masking.

Parameters/features may for example be periodicity/temporal-coherence, envelope modulation depth and shape, interaural coherence and coherence across microphones of the audio signal.

The status of an electrode pulse may be determined based on values of the parameters/features. For example, in a first stage, a set of electrodes could first be identified by computing the parameter/feature value on each electrodes having assigned an electrode pulse and selecting the highest valued electrodes, i.e. the electrodes with the highest parameter/feature values. These selected electrodes would then constitute the electrodes that would best convey the perceptual feature of interest for the user of the cochlear implant system, if masking effects were absent. In a second stage, the masking adjusted energy/charge/level could then be computed for all possible electrodes or for just the subset of highest valued electrodes. These masking adjusted energy/charge/levels would essentially reflect the amount of information transfer that each channel/electrode pulse would be able to transmit up the auditory nerve, thus the salience/strength of the perceptual effect it would elicit, given the level and relative timing the electrode pulse on each electrode. Since the parameter/feature of interest is not directly related to masking adjusted energy/charge/levels, electrodes with high importance values based on parameter/feature of interest may not necessarily have their information reliably transferred up the auditory nerve due to masking. Therefore, an additional process could be introduced whereby the energy/charge of the highest importance valued electrodes is increased, so as to increase their masking-weighted energy/charge values and thus increase the capacity of those electrodes to transmit information up the auditory nerve. The range of possible energy/charge adjustments should be limited to prevent excessively large (and unsafe) changes in pulse energy/charge. The amount of masking adjusted energy/charge/level applied to a given electrode could also be modulated by the parameter/feature value of that electrode, so that electrodes with highest parameter values are adjusted so as to have highest masking adjusted energy/charge/level than electrodes with lower parameter/feature values. Following these energy/charge adjustments, the determination of the masking adjusted energy/charge/level could be applied using all electrodes or just the subset of highest valued electrodes. The result would be that the electrodes with the highest masking adjusted energy/charge/level would be selected for stimulation, whereby some the energy/charge/level on some electrodes may have been boosted to compensate for masking effects.

The processing unit may then be configured to amplify the pulse energy/charge/level of the electrode pulse for boosting the energy level and for compensating for the masking effect, i.e. the cross-electrode interference.

The processing unit may be configured to set the cochlear implant system into a power saving mode by increasing the importance threshold value. By increasing the threshold value more electrode pulses would not be selected by the processor unit. In other words, the processor unit is configured to remove electrode pulses that are assumed to not provide a perceptual benefit, and thus, save power and transmitting fewer pulses.

Definitions

In the present context, the cochlear stimulation system or a hearing aid including the cochlear stimulation system refers to a device, which is adapted to improve and/or augment hearing capability of a user by receiving acoustic signals from the user's surroundings, generating corresponding electric audio signals, possibly modifying the electric audio signals and providing the possibly modified electric audio signals as audible signals to at least one of the user's ears via stimulation provided by an array of electrodes.

More generally, a hearing aid comprises an input transducer for receiving an acoustic signal from a user's surroundings and providing a corresponding input audio signal and/or a receiver for electronically (i.e. wired or wirelessly) receiving an input audio signal, a (typically configurable) signal processing circuit (e.g. a signal processor, e.g. comprising a configurable (programmable) processor, e.g. a digital signal processor) for processing the input audio signal and an output unit for providing an audible signal to the user in dependence on the processed audio signal. The signal processor may be adapted to process the input signal in the time domain or in a number of frequency bands. In some hearing aids, an amplifier and/or compressor may constitute the signal processing circuit. The signal processing circuit typically comprises one or more (integrated or separate) memory elements for executing programs and/or for storing parameters used (or potentially used) in the processing and/or for storing information relevant for the function of the hearing aid and/or for storing information (e.g. processed information, e.g. provided by the signal processing circuit), e.g. for use in connection with an interface to a user and/or an interface to a programming device. In some hearing aids, the output unit may comprise transducer, such as e.g. a vibrator for providing a structure-borne or liquid-borne acoustic signal. In some hearing aids, the output unit may comprise one or more output electrodes for providing electric signals (e.g. a multi-electrode array for electrically stimulating the cochlear nerve).

In some hearing aids, the vibrator may be adapted to provide a structure-borne acoustic signal transcutaneously or percutaneously to the skull bone. In some hearing aids, the vibrator may be implanted in the middle ear and/or in the inner ear. In some hearing aids, the vibrator may be adapted to provide a structure-borne acoustic signal to a middle-ear bone and/or to the cochlea. In some hearing aids, the vibrator may be adapted to provide a liquid-borne acoustic signal to the cochlear liquid, e.g. through the oval window. In some hearing aids, the output electrodes may be implanted in the cochlea or on the inside of the skull bone and may be adapted to provide the electric signals to the hair cells of the cochlea, to one or more hearing nerves, to the auditory brainstem, to the auditory midbrain, to the auditory cortex and/or to other parts of the cerebral cortex.

A 'hearing system' refers to a system comprising one or two hearing aids, e.g. one BTE unit and a cochlear implant, and a 'binaural hearing aid system' refers to a system comprising two hearing aids and being adapted to cooperatively provide audible signals to both of the user's ears. Hearing aid systems or binaural hearing aid systems may further comprise one or more 'auxiliary devices', which communicate with the hearing aid(s) and affect and/or benefit from the function of the hearing aid(s). Auxiliary devices may be e.g. remote controls, audio gateway devices, mobile phones (e.g. SmartPhones), or music players. Hearing aid, hearing aids systems or binaural hearing aid systems may e.g. be used for compensating for a hearing-impaired person's loss of hearing capability and/or augmenting a normal-hearing person's hearing capability and/or conveying electronic audio signals to a person. Hearing aids or hearing aid systems may e.g. form part of or interact with public-address systems, active ear protection systems, handsfree telephone systems, car audio systems, entertainment (e.g. karaoke) systems, teleconferencing systems, classroom amplification systems, etc.

An 'unit' is a device with technical and functional features. The 'unit' is considered to be a device within this disclosure.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 1A to 1C, illustrate examples of a cochlear implant system,

FIGS. 2A and 2B, illustrate a known 'N-of-M' type electrode selection often employed in sound coding strategies, FIGS. 3A-3C, illustrate an example of the processor unit selecting and reserving N number of electrodes of a plurality of electrodes (M), FIG. 5 illustrates an example of an electrode array arranged within a cochlea of a user of the cochlear implant system, FIGS. 6A and 6B illustrate an example of the masking model scheme including spatial masking contributions, FIGS. 7A to 7E illustrate an example of the masking model scheme including temporal masking contributions, FIG. 8 illustrates an example where the masking model scheme includes both the determination of the spatial masking contributions and the determination of the temporal masking contributions, FIGS. 9A to 9D illustrates different examples of the cochlear implant system.

DETAILED DESCRIPTION

Figure 3C:
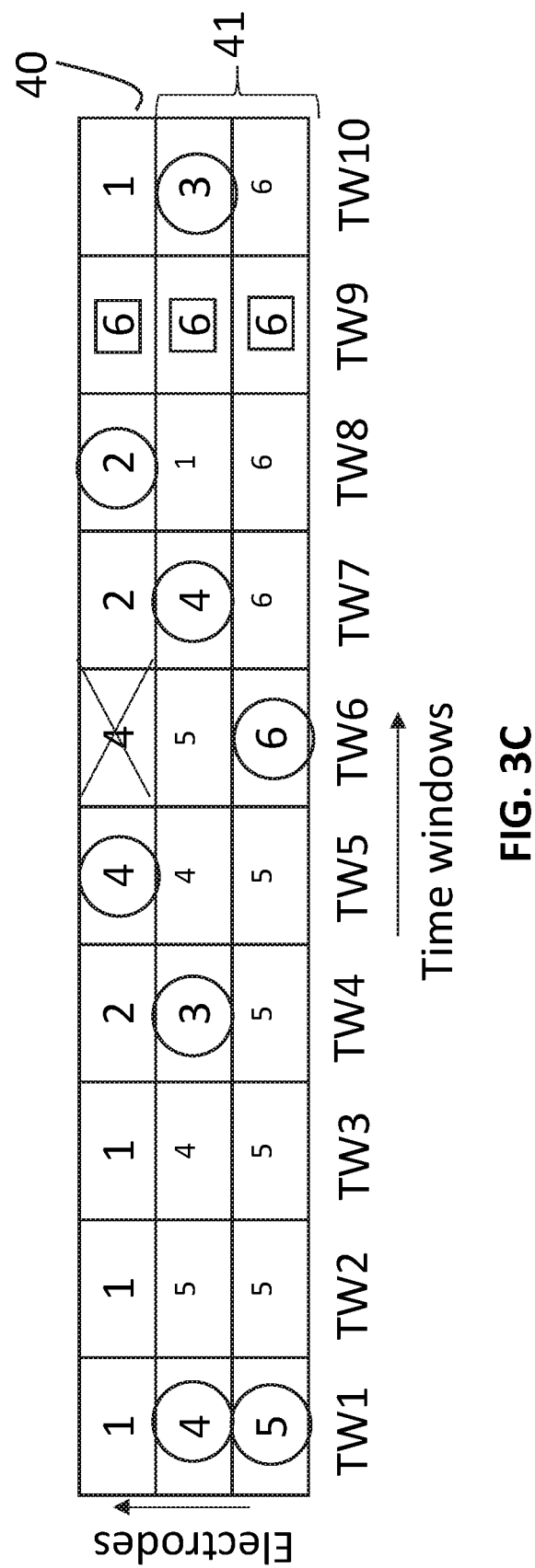

The detailed description set forth below in connection with the appended drawings is intended as a description of various configurations. The detailed description includes specific details for the purpose of providing a thorough understanding of various concepts. However, it will be apparent to those skilled in the art that these concepts may be practiced without these specific details. Several aspects of the apparatus and methods are described by various blocks, functional units, modules, components, circuits, steps, processes, algorithms, etc. (collectively referred to as "elements"). Depending upon particular application, design constraints or other reasons, these elements may be implemented using electronic hardware, computer program, or any combination thereof.

It is intended that the structural features of the devices described above, either in the detailed description and/or in the claims, may be combined with steps of the method for determining Temporal Fine Structure parameter, when appropriately substituted by a corresponding process.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element but an intervening elements may also be present, unless expressly stated otherwise. Furthermore, "connected" or "coupled" as used herein may include wirelessly connected or coupled. As used herein, the term "and/or" includes any and all combinations of one or more of the associated listed items. The steps of any disclosed method is not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the particular features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects.

The claims are not intended to be limited to the aspects shown herein, but is to be accorded the full scope consistent with the language of the claims, wherein reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

FIGS. 1A to 1C illustrate an example of a cochlear implant system 1, comprising a microphone unit 2 configured to receive an acoustical signal and transmit an audio signal based on the acoustical signal. The cochlear implant system 1 includes a processor unit 3 configured to receive the audio signal and process the audio signal into a plurality of electrode pulses and an electrode array 4 including a plurality of electrodes 5 configured to stimulate auditory nerves of a user of the cochlear implant system based on the plurality of electrode pulses.

In FIGS. 1A to 1C the electrode array 4 is arranged within a cochlea 10 of a user of the cochlear implant system 1.

In FIGS. 1A to 1C the processor unit 3 is configured to assign an importance value to one or more electrodes of the plurality of electrodes 5, wherein each of the importance values is determined based on a status of an electrode pulse assigned to the respective electrode. The processing unit 3 is further configured to select a main set of electrodes MS of the plurality of electrodes M during a time window TW, where the importance value of each of the selected electrodes of the main set of electrodes MS is larger or equal to an importance threshold value. The processor unit 3 is configured to activate the electrodes of the main set of electrodes to stimulate auditory nerves based on the electrode pulses of the plurality of electrode pulses, and reserve the electrodes of the main set of electrodes MS into a reserving mode during a reservation period.

In FIGS. 1A and 1B, the cochlear implant system 1 includes an external part 20 arranged on the head of the user of the cochlear implant system 1 and an implant part 30 arranged under the skin 50 of the user. The external part 20 includes a first inductive interface 21 and the implant part 30 includes a second inductive interface 31, wherein the external part 20 is configured to communicate via the first inductive interface 21 to the second inductive interface 31 of the implant part 30. The implant part 30 is connected to the electrode array 10.

In FIG. 1A, the processor unit 3 is arranged within the external part 20, and the external part 20 includes a memory unit 22. In another example, the memory unit 22 may be arranged within the implant part 30. The memory unit is configured to store the importance values of the one or more electrodes, and the processor unit may be configured to update the importance value continuously based on changes to the status of an electrode pulse assigned to the respective electrode.

In FIG. 1B, the processor unit 3 is arranged within the implant part 30.

In FIG. 1C, the cochlear implant system 1 includes an implant part 30, wherein the implant part 30 includes the microphone 2, the processor unit 3 and the memory unit 22. Optionally, the implant part may include a communication interface configured for communicating inductively or via an electromagnetic link, such as an RF link, with an external device, such as a remote processor unit, a smartphone or any computable device.

FIGS. 2A and 2B illustrate a known 'N-of-M' type electrode selection often employed in sound coding strategies that generate electrode pulses at a stimulation rate that is either fixed or variable over-time and across electrodes. In cochlear implant systems with fixed stimulation rate, the time windows (TW1-TW10) within which N-of-M selection is performed are set so that is possible for an equal number of events (i.e. pulses) to be present on each electrode, and no electrode enjoys a selection advantage at any given time due to the stimulation rate at which events occur. However, when sound coding strategies are instead based on events that occur at stimulation rates that vary over-time and across electrodes, electrodes with higher event rates may receive a selection advantage over low-rate electrodes by virtue of containing more events in the time windows within which N-of-M selection is executed.

In FIG. 2A, the total electrodes of the plurality of electrodes is set to 3 (M) and a subset of the plurality of electrodes is set to 2 (N). In this example, the selection of the electrodes is applied to a fixed-rate sound coding strategy. The stimulation rate is such that each time windows (TW1-TW10) comprises an event, i.e. an electrode pulse, on each electrodes 5. The abscissa denotes the time windows while the ordinate corresponds to electrode index. The value displayed in each electrode cell indicates the importance value of the contained active event. Electrodes selected in each time windows are marked with a circle. For example, in first time window TW1 two electrodes are selected with an importance value of 4 and 5, respectively. The two electrodes are selected because they both have the highest importance value of the three electrodes. The selections of the two electrodes are preserved throughout the time windows TW1 to TW4, and in time window TW5, a third electrode is selected over one of the two previously selected electrodes. Again, the importance value of the two selected electrodes are the highest of the three electrodes. The selected electrodes are preserved in time window TW6.

In FIG. 2B, the total electrodes of the plurality of electrodes is set to 3 and a subset of the plurality of electrodes is set to 2. In this example, the selection of the electrodes is applied to a variable-rate sound coding strategy, where the stimulation rates increase with electrode index. The abscissa denotes the time epoch while the ordinate corresponds to electrode index, and where '-' indicates the absence of an event, i.e. an electrode pulse. The value displayed in each electrode-epoch cell indicates the importance value of the contained event. This illustrated scenario could represented, for example, conditions where there is speech with high energy low frequency content in the present of higher frequency noise. Electrodes selected in each epoch, i.e. time window, are marked with a circle. In this example, there are time windows when low-importance events on the high-rate channel are selected purely because there are no events on the other channels. These low importance pulses would potentially interfere the more important events on other electrodes indicated with the broken-line boxes.

FIGS. 3A-3C, illustrate an example of the processor unit selecting and reserving N number of electrodes of a plurality of electrodes (M) with a variable-rate sound coding strategy and where the stimulation rates increase with electrode index. Furthermore, FIG. 3A-3C illustrates how the disclosure is solving the problem of the known 'N-of-M' type electrode selection scheme illustrated in FIGS. 2A and 2B.

In FIG. 3A, the abscissa denotes the time epoch while the ordinate corresponds to electrode index, with indicating the absence of an event. The value displayed in each electrode-epoch cell indicates the importance value of the electrode pulses. The selected electrodes in each time window are marked with a circle, and those which are in reserved mode are indicated by a box around '-', and those blocked from selection by another electrode in a reserved mode are indicated with a cross.

In first time window TW1, the processor unit 3 has selected the two electrodes which have an importance value which is either equal to or larger than an importance threshold value. The selected electrodes are part of a main set (MS, 41) of electrodes of the plurality of electrodes (4,5). In this example, the importance threshold value is 3. In time windows TW2 and TW3, the reserved electrodes are not active, that means no electrode pulses are assigned to those electrodes. During these time windows, i.e. TW2 and TW3, the processor unit 3 is not allowed to select the electrode which is active because the importance value of the electrode/electrode pulse is below the importance threshold value. However, if the importance value of the electrode not being reserved had an importance value which is equal to or above the importance threshold value, e.g. see time windows TW5 and TW6, then the processor unit 3 would not be allowed to select the electrode. The reservation of the electrodes is denoted as being 'hard'-reserved.

In time window TW4, the processor unit 3 is configured to select a subset 42 of electrodes of the main set 41 of electrodes, because the importance value of the selected electrode is larger or equal to the importance threshold value, During time window TW1, the processor unit 3 activates two electrodes 5 of the electrode array 4 for stimulating the auditory nerves of the user's cochlea. In time window TW4, only one electrode is selected for stimulation of the auditory nerves, and so on for the other time windows.

In FIG. 3B, the importance value registered during the time window that electrode entered the reserved mode is held over the duration of the reservation period. The abscissa denotes the time epoch while the ordinate corresponds to channel/electrode index, with indicating the absence of an event. The value displayed in each channel/electrode-epoch cell indicates the 'importance' value of the contained event; larger font numbers indicate the importance value of event channels while small font-sized numbers indicate importance to electrodes in a reservation mode. Electrodes selected in each time window are marked with a circle, those in reserved mode are indicated by the small font-sized numbers, and those blocked from selection by another electrode in a reserved mode are indicated with a 'x'. In this example, the processor unit 3 is configured to select a subset 42 of electrodes of the plurality of electrodes (40,5) and/or of the main set 41 of electrodes during the reservation period, see e.g. time windows TW4 to TW7, and TW10, wherein each of the electrodes of the subset of electrodes has an importance value that is larger or equal to the importance threshold value. In for example time window TW6, the processor unit 3 has selected two electrodes, one from the main set 41 and one from the plurality 40 of electrodes which includes electrodes that are not part of the main set of electrodes. In TW5, the processor unit 3 has selected one electrode which is part of the plurality of electrodes 40.

The processor unit 3 is configured to activate the electrodes 5 of the subset 42 of electrodes to stimulate auditory nerves based on the electrode pulses of the plurality of electrode pulses.

In FIG. 3C, the importance value of a reserved electrode is updated on each time window (TW1-TW10) during the duration of a reservation period. The abscissa denotes the time window while the ordinate corresponds to electrode index. The value displayed in each electrode-time window cell indicates the importance value of the contained electrode pulse, i.e. the event; larger font numbers indicate the importance value of electrode pulses while small font-sized numbers indicate importance to electrode pulses in a reservation mode. To illustrate the difference between this implementation, and the one in FIG. 3B, electrodes that have been additionally selected or rejected in this implementation are marked with a circle or cross respectively.

Time window, TW9, of FIG. 3c, an example of a tie-break is seen between three active electrodes pulses carrying electrodes having the same importance metric value. Only a subset of those electrodes can be selected. In this scenario, a 'tie-breaker' importance value could be assigned by the processor unit 3 to the electrodes being part of the tie-breaker. The tie-breaker importance value must be different from the importance value or from the importance value previously defined, e.g. in time window TW8, and could include: channel center frequency, pulse energy, Signal-to-noise-ratio, interaural coherence, periodicity, etc.

The tie-breaker importance value of the electrodes is not shown in FIG. 3c.

The processor unit 3 may be configured to update the main set 41 of electrodes by adding a new electrode 5 of the plurality of electrodes 4 to the main set 41 of electrodes where the importance value of the new electrode is larger or equal to the first threshold importance value (Thimp_1).

The processor unit 3 may be configured to renew the reservation period of an electrode 5 of the main set 41 of electrodes when a new electrode pulse generating event occurs on that electrode 5 with an importance value that is greater than or equal to the importance threshold value (Thimp).

Figure 4:
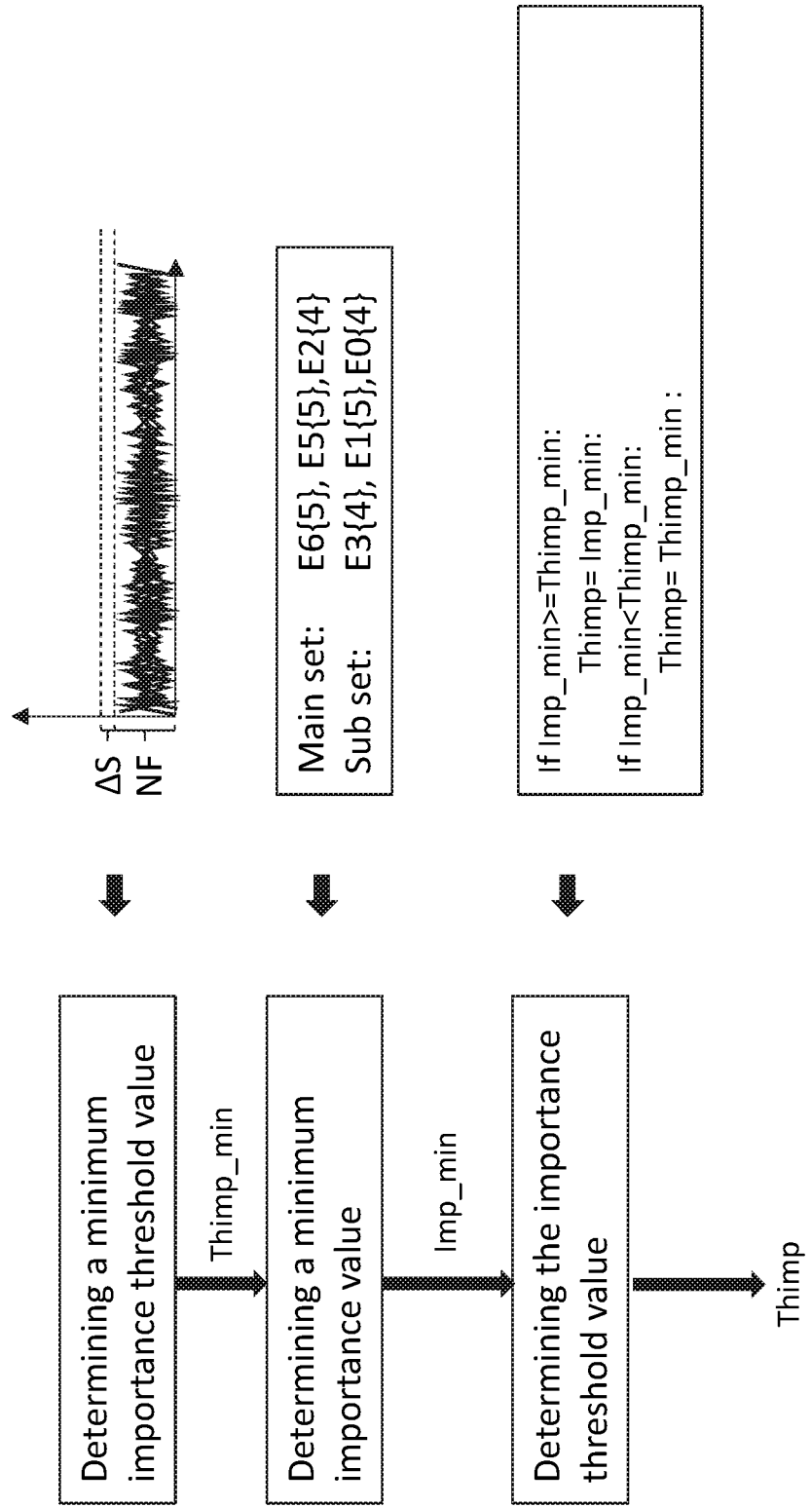
FIG. 4 illustrates an example of determining the importance threshold value.

The processor unit 3 may be configured to remove an electrode 5 from the main set 41 of electrodes when the reservation period of that electrode 5 has expired, and before that reservation period could be renewed FIG. 4 illustrates an example of determining the importance threshold value (Thimp). A minimum importance threshold value (Thimp_min) is determined by summing a noise floor NF of the electrode array 4 (i.e. of the cochlear implant system 1) and a safety margin $\Delta S$ of 1 to 3 dB. The noise estimation NF may be in average 20 dB SPL and the chosen safety margin $\Delta S$ is 3 dB, and the resulting minimum importance threshold value (Thimp_min) is set to 23 dB SPL.

The minimum importance threshold value (Thimp_min) may be any measurable parameter of an electrode pulse, such as a center frequency, signal-to-noise ratio, noise floor, and electrode pulse energy.

Then, a minimum importance value (Imp_min) of the subset 42 and/or main set 41 of electrodes may be determined based on the assigned importance value of the subset 42 and/or main set 41 of electrodes, respectively. In this example, the electrode indexes which are part of the main set 41 are E6, E5 and E2, and the importance value of each electrodes is 5, 5, and 4, respectively. The electrode indexes which are part of the sub set 42 are E3, E1 and E0, and the importance value of each electrodes is 4, 5, and 4, respectively.

Then, the importance threshold value (Thimp) may be equal to the minimum importance value (imp_min) if the minimum importance value (imp_min) is larger or equal to the minimum importance threshold value (Thimp_min).

The importance threshold value (Thimp) may be equal to the minimum importance threshold value (Thimp_min) if the minimum importance value (imp_min) is smaller than the minimum importance threshold value (Thimp_min).

FIG. 5 illustrates an example of an electrode array 4 arranged within a cochlea 10 of the user of the cochlear implant system 1. The cochlea includes multiple auditory nerves 11 which are to be stimulated by the electrodes (5A, 5B) of the electrodes array 4. In this example the electrodes (5A,5B) produce an excitation overlap 61 which produces significant across-electrode interferences, i.e. masking, whereby stimulation on one of the two electrodes (5A,5B) consumes some of the neural resources of the auditory nerves at the site of neighbouring electrodes (5A,5B), thus disrupting the neural excitation elicited by stimulation.

FIGS. 6A and 6B illustrate an example of the masking model scheme including spatial masking contributions. In FIG. 6A the processor unit 3 has selected and activated two electrodes (5A,5B) within a first time window (TW), and in FIG. 6B, the processor unit 3 has selected and activated two electrodes (5A,5B) within a second time window (TW). The spatial separation between the two electrodes activated within the first time window is less than the spatial separation between the two electrodes activated within the second time window. The spatial separation is determined based on the respective stimulation levels of the two electrodes, and in the second time window (TW) the processor unit 3 has reduced at least one of the two electrodes's stimulation level for reducing the spatial masking contributions. Alternatively, the spatial separation could be increased by selecting electrodes (5A,5C) which physically are arranged further away from each other. In FIG. 6A, the activation of the two electrodes (5A,5B) generates excitation overlap 61 which results in cross-electrode interference. In FIG. 6B, the spatial separation has increased and which results in elimination of the excitation overlap 61. The change in the spatial separation is provided by the masking model scheme which determines spatial masking contributions of each of the two electrode pulses of the two electrodes (5A, 5B).

Figure 7E:
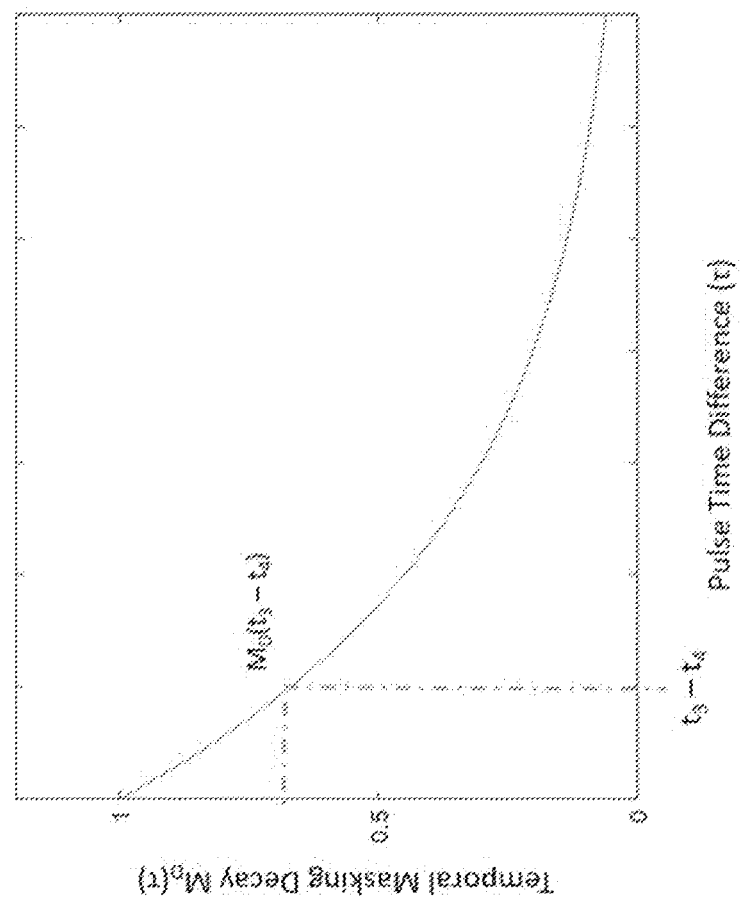

FIGS. 7A to 7E illustrate an example of the masking model scheme including temporal masking contributions, more specifically, cross-electrode interference between electrodes (5A, 5B) is determined by the temporal masking contributions of each of the two electrode pulses of the two electrodes (5A, 5B). In FIGS. 7B and 7C the electrodes to be activated are the same and are seen in FIG. 7A. In FIG. 7A, the excitation overlap 61 is seen for the case where a pulse time difference is $\Delta T1$ and where a time delay $\Delta TW$ is zero between a first time window TW1 and a second time window TW2. In both time windows, the processor unit 3 is configured to select a main set of electrodes 41 of the plurality of electrodes, where the importance value of each of the selected electrodes of the main set 41 of electrodes or subset of electrodes 40 is larger or equal to an importance threshold value.

In FIG. 7B, the pulse time difference $\Delta T1$ and $\Delta T2$ is between a first time and a second time of the electrode pulses assigned to the two electrodes (5A,5B), respectively. The processor unit 3 increases the pulse time difference $\Delta T1$ to $\Delta T2$ and which results in a reduction of the cross-electrode interference. The increase of the pulse time difference $\Delta T$ is based on the masking model scheme which determines temporal masking contributions of each of the two electrode pulses of the two electrodes (5A, 5B).

FIG. 7C illustrates an example where a time delay $\Delta TW1$ between the first time window TW1 and the second time window TW2 is set to zero. In this example, the cross-electrode interference is high. Then, the processor unit 3 increases the time delay between the two time windows (TW1, TW2) based on the masking model scheme and which results in a reduced cross-electrode interference between the activated electrodes (5A, 5B).

Figure 7D:
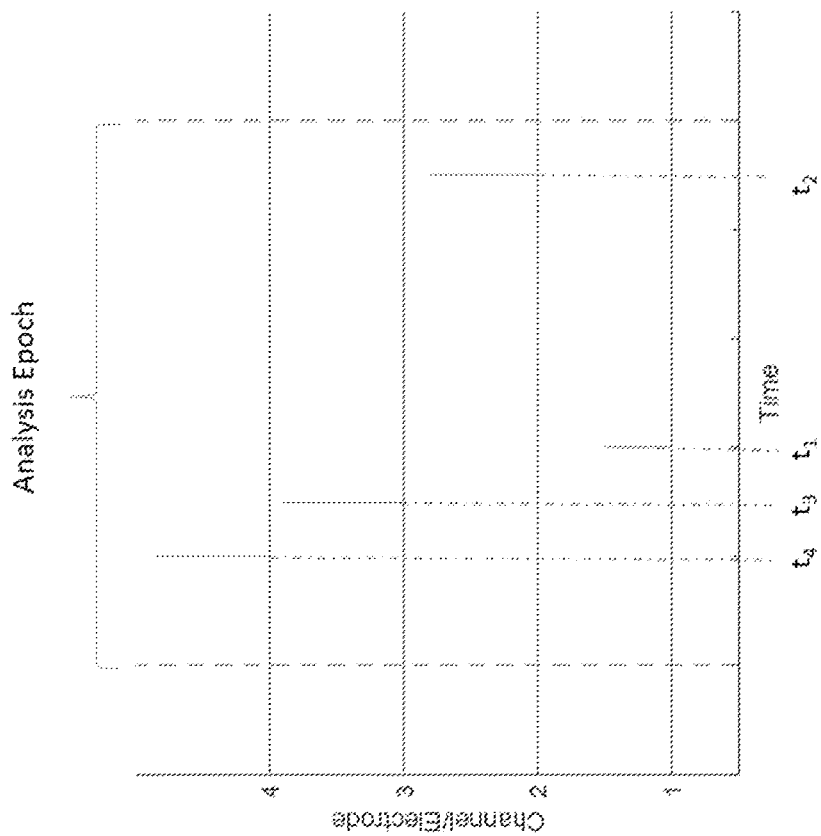

FIG. 7D illustrates an example of an electrodogram of electrode pulse sequence within a time window, and FIG. 7E illustrates an example of a temporal masking decay function MD(t3-t4) as a function of the time difference between a leading electrode pulse, e.g. electrode pulse t3 and a masked (lagging) pulse, e.g. electrode pulse t4. The temporal masking decay function MD(t3-t4) is associated with the masking of the pulse on channel/electrode 3 by the pulse on channel/electrode 4.

FIG. 8 illustrates an example where the masking model scheme includes both the determination of the spatial masking contributions and the determination of the temporal masking contributions. In another example the processor unit 3 is configured to determine the importance value based on either or both spatial masking contributions and temporal masking contributions. The processor unit 3 may shift between using either both contributions or just one of the contributions, and where the shift is determined based on the number of selected electrodes of the main set of electrodes. For example, if the processor unit 3 selects to include temporal masking contribution and no electrodes has an importance value which is above an importance threshold value, then the processor unit 3 may shift to use both temporal and spatial masking contributions or to use spatial masking contribution alone.

FIGS. 9A to 9D illustrates different examples of the cochlear implant system 1 including a sensor (50A-50D) for measuring parameters to be used in determine the status of the electrode pulses. The measurements may be performed during fitting and/or during operation of the cochlear implant system 1. In FIG. 9A, the electrode array 4 is arranged within the cochlea 10 of the user. The electrode array 4 includes both the electrodes 5 configured for stimulating the auditory nerves 11 of the cochlea 10 and the sensors (50A-50D). In FIG. 9B, the electrode array 4 is a flexible printed circuit board 51 or a flexible substrate 51 which includes a first layer 52, a second layer 53 and a third layer 54. The first layer 52 includes the plurality of electrodes 5, the second layer 53 is an insulator layer, and the third layer 53 includes the sensors (50A-50D). The pulse energy level of each electrode is determined by the processor unit 3 alone or based on measurements performed by the sensors (50A-50D) or the electrodes 5. The sensors (50A-50D) are connected to the processor unit 3 and configured to measure the stimulation provided by the electrodes. The measured stimulation may include the measured parameters, such as the pulse energy level and/or a noise floor level, and the measured parameters are transferred to the processor unit 3. The processor unit 3 may be configured to determine a signal-to-noise ratio of an electrode 5 based on the measured parameters.

Optionally, the second layer may be removed for reducing the thickness of the electrode array 4.

The sensors (50A-50D) and/or the electrodes 5 may be used for performing eCAP measurements.

In FIGS. 9C and 9D, the sensor 50 is arranged on the implant part 30 or on the external part 20. In this example, the sensor is configured to measure cognitive load of the user, and the processor unit is configured to control the cross-electrode interference based on the measured cognitive load. The sensor may be part of the electrode array 4, the implant part 30 or the external part 20. The sensor may include one or more electrode pads made of IrO2.

The invention claimed is:

1. A cochlear implant system comprising:
a microphone unit configured to receive an acoustical signal and transmit an audio signal based on the acoustical signal,
a processor unit configured to receive the audio signal and process the audio signal into a plurality of electrode pulses,
an electrode array including a plurality of electrodes configured to stimulate auditory nerves of a user of the cochlear implant system based on the plurality of electrode pulses, and wherein the processor unit is configured to:
assign an importance value to one or more electrodes of the plurality of electrodes, wherein each of the importance values is determined based on a status of an electrode pulse assigned to the respective electrode,
select a main set of electrodes of the plurality of electrodes during a time window, where the importance value of each of the selected electrodes of the main set of electrodes is larger or equal to an importance threshold value,
activate the electrodes of the main set of electrodes to stimulate auditory nerves based on the electrode pulses of the plurality of electrode pulses, and
select the electrodes of the main set of electrodes from among the plurality of electrodes as reserved electrodes to be placed into a reserved mode during a reservation period, wherein the specific selection of electrodes as the reserved electrodes influences a selection of electrodes to be activated during a subsequent time window during the reservation period by virtue of the reserved electrodes blocking activation of at least one other electrode of the plurality of electrodes that would otherwise be selected for activation based on the corresponding importance value.

2. A cochlear implant system according to claim 1, wherein the status of the electrode pulse of the plurality of electrode pulses is determined based on a masking model scheme of across-electrode interferences imposed on that electrode pulse by other electrode pulses of the plurality of electrode pulses.

3. A cochlear implant system according to claim 2, wherein the status of the electrode pulse of an electrode of the plurality of electrodes includes a determined amount of across-electrode interference induced on the electrode pulse of the electrode by one or more electrode pulses of other electrodes of the plurality of electrodes based on the masking model scheme, wherein the masking model scheme comprises:
determining spatial masking contributions of each of the one or more electrode pulses of the other electrodes induced on the electrode pulse of the electrode based on a spatial separation between the electrode and each of the other electrodes.

4. A cochlear implant system according to claim 3, wherein the masking model scheme comprises both the determining of the spatial masking contributions and the determining of temporal masking contributions.

5. A cochlear implant system according to claim 4, wherein the determined spatial masking contribution from each of the electrode pulses of the other electrodes is multiplied by a temporal masking decay function including the pulse time difference between the electrode pulse of the electrode and each of the electrode pulses of the other electrode.

6. A cochlear implant system according to claim 5, wherein the temporal masking decay function is an exponential factor including a time constant and/or the pulse time difference, and wherein the time constant is either the same or different for each of the electrodes of the plurality of electrodes.

7. A cochlear implant system according to claim 2, wherein the status of the electrode pulse of an electrode of the plurality of electrodes includes a determined amount of across-electrode interference induced on the electrode pulse of the electrode by one or more electrode pulses of other electrodes of the plurality of electrodes based on the masking model scheme, wherein the masking model scheme comprises:
determining temporal masking contributions of each of the one or more electrode pulses of the other electrodes induced on the electrode pulse of the electrode based on a pulse time difference between a first time of the electrode pulse of the electrode and a second time of each of the one or more electrode pulses of the other electrodes, wherein the second time is preceding to the first time.

8. A cochlear implant system according to claim 7, wherein the processing unit is configured to control the cross-electrode interference by changing the first time of the electrode pulse of the electrode and/or the preceding time of each of the one or more electrode pulses of the other electrodes, or by applying a time delay between a first time window and a second time window, where in both of the time windows the processor unit is configured to select a subset of electrodes of the plurality of electrodes and/or to select electrodes of the main set of electrode of the plurality of electrodes.

9. A cochlear implant system according to claim 1, comprising a memory unit which is configured to store the importance values of the one or more electrodes, and the processor unit is configured to update the importance value continuously based on changes to the status of an electrode pulse assigned to the respective electrode.

10. A cochlear implant system according to claim 9,
wherein the processor unit is configured to select for activation a subset of the electrodes of the main set of electrodes selected as the reserved electrodes during the subsequent time window of the reservation period, and no other electrodes of the plurality of electrodes are allowed to be selected for activation during the subsequent time window, and
wherein each of the electrodes of the subset of electrodes has an importance value during the subsequent time window that is larger or equal to the importance threshold value, and
wherein the processor unit is configured to activate the electrodes of the subset of electrodes to stimulate auditory nerves based on the electrode pulses of the plurality of electrode pulses.

11. A cochlear implant system according to claim 9,
wherein the processor unit is configured to select for activation a subset of electrodes of the plurality of electrodes during the subsequent time window of the reservation period,
wherein each of the electrodes of the subset of electrodes has an importance value during the subsequent time window that is larger or equal to the importance threshold value, wherein the subset of electrodes includes a non-reserved electrode, the non-reserved electrode being one of the plurality of electrodes not selected as one of the reserved electrodes, the non-reserved electrode being assigned a higher importance value during the subsequent time window than the most-recently assigned importance value of at least one of the reserved electrodes, and wherein the processor unit is configured to activate the electrodes of the subset of electrodes to stimulate auditory nerves based on the electrode pulses of the plurality of electrode pulses.

12. A cochlear implant system according to claim 1, wherein the processor unit is configured to sample the audio signal within a frequency range, and wherein the status of the electrode pulse of the plurality of electrode pulses includes:
    an estimated pulse energy level within a subset of frequencies of the frequency range, an estimated signal-to-noise ratio of the sampled audio signal within a subset of frequencies of the frequency range,
    a periodicity in the audio signal within a subset of frequencies of the frequency range, audio coherence across the electrodes of the plurality of the electrodes, and/or
    an audio coherence between audio signals received by two or more microphones of the microphone unit.

13. A cochlear implant system according to claim 12, wherein the processing unit is configured to set the cochlear implant system into a power saving mode by increasing the importance threshold value, where the importance threshold value is:
    a minimum allowable masking-weighted energy/charge/level value,
    a minimum signal-to-noise ratio of an electrode pulse,
    a minimum estimated pulse energy level of an electrode pulse,
    a minimum value of an auto-correlation amplitude, or
    a minimum interaural coherence value.

14. A cochlear implant system according to claim 1,
    wherein the processor unit is configured to select for activation a subset of the electrodes of the main set of electrodes selected as the reserved electrodes during the subsequent time window of the reservation period and no other electrodes of the plurality of electrodes are allowed to be selected for activation during the subsequent time window, and
    wherein each of the electrodes of the subset of electrodes has an importance value during the subsequent time window that is larger or equal to the importance threshold value, and
    wherein the processor unit is configured to activate the electrodes of the subset of electrodes to stimulate auditory nerves based on the electrode pulses of the plurality of electrode pulses.

15. A cochlear implant system according to claim 1,
    wherein the processor unit is configured to select for activation a subset of electrodes of the plurality of electrodes during the subsequent time window of the reservation period,
    wherein each of the electrodes of the subset of electrodes has an importance value during the subsequent time window that is larger or equal to the importance threshold value,
    wherein the subset of electrodes includes a non-reserved electrode, the non-reserved electrode being one of the plurality of electrodes not selected as one of the reserved electrodes, the non-reserved electrode being assigned a higher importance value during the subsequent time window than the most-recently assigned importance value of at least one of the reserved electrodes, and
    wherein the processor unit is configured to activate the electrodes of the subset of electrodes to stimulate auditory nerves based on the electrode pulses of the plurality of electrode pulses.

16. A cochlear implant system according to claim 1, wherein the importance threshold value is determined as following;
    determining a minimum importance threshold value,
    determining a minimum importance value of the subset and/or main set of electrodes,
    determining the importance threshold value as being equal to the minimum importance value if the minimum importance value is larger or equal to the minimum importance threshold value, or determining the importance threshold value as being equal to the minimum importance threshold value, if the minimum importance value is smaller than the minimum importance threshold value.

17. A cochlear implant system according to claim 1, wherein the processor unit is configured to update the main set of electrodes by:
    adding a new electrode of the plurality of electrodes to the main set of electrodes where the importance value of the new electrode is larger or equal to the threshold importance value,
    renewing the reservation period of an electrode of the main set of electrodes when a new electrode pulse generating event occurs on that electrode with an importance value that is greater than or equal to the importance threshold value; and/or
    removing an electrode from the main set of electrodes when the reservation period of that electrode has expired, and before that reservation period could be renewed.

18. A cochlear implant system comprising:
    a microphone unit configured to receive an acoustical signal and transmit an audio signal based on the acoustical signal,
    a processor unit configured to receive the audio signal and process the audio signal into a plurality of electrode pulses,
    an electrode array including a plurality of electrodes configured to stimulate auditory nerves of a user of the cochlear implant system based on the plurality of electrode pulses, and wherein the processor unit is configured to:
    assign an importance value to one or more electrodes of the plurality of electrodes, wherein each of the importance values is determined based on a status of an electrode pulse assigned to the respective electrode,
    select a main set of electrodes of the plurality of electrodes during a time window, where the importance value of each of the selected electrodes of the main set of electrodes is larger or equal to an importance threshold value,
    activate the electrodes of the main set of electrodes to stimulate auditory nerves based on the electrode pulses of the plurality of electrode pulses, and
    reserve the electrodes of the main set of electrodes into a reserved mode during a reservation period,
    wherein the status of the electrode pulse of the plurality of electrode pulses is determined based on a masking model scheme of across-electrode interferences imposed on that electrode pulse by other electrode pulses of the plurality of electrode pulses, wherein the status of the electrode pulse of an electrode of the plurality of electrodes includes a determined amount of across-electrode interference induced on the electrode pulse of the electrode by one or more electrode pulses of other electrodes of the plurality of electrodes based on the masking model scheme, wherein the masking model scheme comprises:

determining spatial masking contributions of each of the one or more electrode pulses of the other electrodes induced on the electrode pulse of the electrode based on a spatial separation between the electrode and each of the other electrodes, and wherein the processor unit is configured to determine the status of an electrode pulse, by determining either a masking adjusted energy/charge/level including an estimated pulse energy/charge/level of the electrode pulse minus the amount of across-electrode interference induced to the electrode pulse from the one or more electrode pulses of the other electrodes, or a masking adjusted energy/charge/level that comprises the estimated pulse energy/charge/level of that electrode pulse multiplied by an across-electrode interference scaling factor that includes an effective energy/charge/level of the electrode pulse after considering the amount of across-electrode interference induced to the electrode pulse from the one or more electrode pulses of the other electrodes, whereby the effective energy/charge/level provides an estimate of the energy/charge/level that would yield the same amount of activity in the auditory nerve as the pulse of interest, if across-electrode interference was absent.

19. A cochlear implant system according to claim 18, wherein the processor unit is configured to select electrodes of the main set of electrodes or of the subset of electrodes which results in a total masking-adjusted/weighted energy/charge/ level which is maximized, and where the total masking-adjusted/weighted energy/charge/ level includes a summation of the masking-adjusted/weighted energy/charge/ level of each of the electrode pulses of the selected electrodes.

20. A cochlear implant system according to claim 18, wherein the processing unit is configured to amplify the pulse energy/charge/level of the electrode pulse.

* * * * *